(12) United States Patent
Kurokawa et al.

(10) Patent No.: US 9,410,176 B2
(45) Date of Patent: Aug. 9, 2016

(54) METHOD FOR PRODUCING PROTEINS

(75) Inventors: Megumi Kurokawa, Tokyo (JP); Yoko Hayashi, Takasaki-shi-Gunma (JP); Masayoshi Tsukahara, Tokyo (JP)

(73) Assignees: Inter-University Research Institute Corporation Research Organization of Information and Systems, Tokyo (JP); KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 13/994,178

(22) PCT Filed: Dec. 14, 2011

(86) PCT No.: PCT/JP2011/078938
§ 371 (c)(1),
(2), (4) Date: Jun. 14, 2013

(87) PCT Pub. No.: WO2012/081629
PCT Pub. Date: Jun. 21, 2012

(65) Prior Publication Data
US 2013/0273604 A1    Oct. 17, 2013

(30) Foreign Application Priority Data
Dec. 15, 2010  (JP) .................... 2010-279850

(51) Int. Cl.
| | |
|---|---|
| *C12N 15/85* | (2006.01) |
| *C12P 21/00* | (2006.01) |
| *C07K 16/00* | (2006.01) |
| *C12P 21/02* | (2006.01) |
| *C07K 16/28* | (2006.01) |

(52) U.S. Cl.
CPC ............... *C12P 21/00* (2013.01); *C07K 16/00* (2013.01); *C07K 16/2896* (2013.01); *C12N 15/85* (2013.01); *C12P 21/02* (2013.01); *C07K 2317/14* (2013.01); *C12N 2800/107* (2013.01); *C12N 2800/90* (2013.01)

(58) Field of Classification Search
None
See application file for complete search history.

(56) References Cited

U.S. PATENT DOCUMENTS

| | | | | |
|---|---|---|---|---|
| 6,096,505 | A * | 8/2000 | Selby et al. | ......... 435/6.16 |
| 2003/0037346 | A1 | 2/2003 | Craig et al. | |
| 2004/0242512 | A1 | 12/2004 | Misawa et al. | |
| 2010/0077495 | A1 * | 3/2010 | Davis et al. | ............ 800/14 |
| 2010/0129914 | A1 | 5/2010 | Hamaguchi et al. | |
| 2010/0311116 | A1 | 12/2010 | Wurm et al. | |
| 2011/0045532 | A1 | 2/2011 | Kawakami et al. | |
| 2012/0196327 | A1 | 8/2012 | Kurokawa et al. | |

FOREIGN PATENT DOCUMENTS

| | | |
|---|---|---|
| JP | 532188 A | 4/2003 |
| WO | 01/29204 A2 | 4/2001 |
| WO | 2008/072540 A1 | 6/2008 |
| WO | 2010036976 A2 | 4/2010 |

OTHER PUBLICATIONS

Sallam et al., Gene, 2007, vol. 386, pp. 173-182.*
Serum-free Media for Cell Culture, 2009, pp. 1-56.*
Koga et al., Developmental Dynamics, 2008, vol. 237, pp. 2466-2474.*
Plotkin et al., Nat Rev Genet, 2010, col. 12, pp. 32-42.*
Westwood, et al.; "Improved Recombinant Protein Yield Using a Codon Deoptimized DHFR Selectable Marker in a CHEF1 Expression Plasmid, Biotechnology Progress, Published Oct. 14, 2010", vol. 26, No. 6, pp. 1558-1566.
Sumiyama, et al.; "New Methods for Mouse Transgenesis with the Tol2 Transposable Element, Experimental Medicine", Published 2010, vol. 28, No. 16, pp. 2653-2660.
Yagita, et al.; "Real-Time Monitoring of Circadian Clock Oscillations in Primary Cultures of Mammalian Cells Using Tol2 Transpoon-Mediated Gene Transfer Strategy", BMC Biotechnology, Published 2010, vol. 10, No. 3, pp. 1-7.
Wu, et al.; "*PiggyBac* is a Flexible and Highly Active Transposon as Compared to *Sleeping Beauty, Tol2*, and *Mos1* in Mammalian Cells", Proceedings of the National Academy of Sciences USA, Published Oct. 10, 2006, vol. 103, No. 41, pp. 15008-15013.
Urasaki, et al.; "Functional Dissection of the *Tol2* Transposable Element Identified the Minimal *cis*-Sequence and a Highly Repetitive Sequence in the Subterminal Region Essential for Transposition", Genetics, Published Oct. 2006, vol. 174, pp. 639-649.
Koga, et al.; "Transposable Element in Fish", Nature, Published Sep. 5, 1996, vol. 383, p. 30.
Ivics, et al.; "Molecular Reconstruction of *Sleeping Beauty*, a *Tc1*-like Transposon from Fish, and Its Transposition in Human Cells", Cell, Published Nov. 14, 1997, vol. 91, pp. 501-510.
Miskey, et al.; "The Frog Prince: a Reconstructed Transposon from *Rana Pipiens* with High Transpositional Activity in Vertebrate Cells", Nucleic Acids Research, Published 2003, vol. 31 No. 23, pp. 6873-6881.

(Continued)

*Primary Examiner* — Michele K Joike
*Assistant Examiner* — Mindy G Brown
(74) *Attorney, Agent, or Firm* — Sughrue Mion, PLLC

(57) ABSTRACT

This invention relates to a method for producing a protein of interest, comprising introducing an expression vector which comprises a gene fragment comprising a DNA encoding the protein of interest and a selectable marker gene and also comprises a pair of transposon sequences at both terminals of the gene fragment, into a suspension mammalian cell; integrating the gene fragment inserted between the pair of transposon sequences into a chromosome of the mammalian cell; obtaining a suspension mammalian cell producing the protein of interest; and suspension-culturing the suspension mammalian cell, and a suspension mammalian cell which expresses the protein of interest by the method.

10 Claims, 1 Drawing Sheet

(56) References Cited

OTHER PUBLICATIONS

Fraser, et al.; "Precise Excision of TTAA-Specific Lepidopteran Transposons *PiggyBac* (IFP2) and *Tagalong* (TFP3) from the Baculovirus Genome in Cell Lines from Two Species of *Lepidoptera*", Insect Molecular Biology, Published 1996, vol. 5, pp. 141-151.

Kawakami, et al.; "Transposition of the *Tol2* Element, an *Ac*-Like Element From the Japanese Medaka Fish *Oryzias Latipes*, in Mouse Embryonic Stem Cells", Genetics, Published Feb. 2004, vol. 166, pp. 895-899.

Balciunas, et al.; "Harnessing a High Cargo-Capacity Transposon for Genetic Applications in Vertebrates", Public Library of Science Genetics, Published Nov. 2006, vol. 2, Issue 11, pp. 1715-1724.

Luo, et al.; "Chromosomal Transposition of a Tc1/Mariner-Like Element in Mouse Embryonic Stem Cells", Proceedings of the National Academy of Sciences USA, Published Sep. 1998, vol. 95, pp. 10769-10773.

Fischer, et al.; "Regulated Transposition of a Fish Transposon in the Mouse Germ Line", Proceedings of the National Academy of Sciences USA, Published Jun. 5, 2001, vol. 98, No. 12, pp. 6759-6764.

Dupuy, et al.; "Mammalian Mutagenesis Using a Highly Mobile Somatic *Sleeping Beauty* Transposon System", Nature, Published Jul. 14, 2005, vol. 436, pp. 221-226.

Cadinanos, et al.; "Generation of an Inducible and Optimized *PiggyBac* Transposon System", Nucleic Acids Research, Published Jun. 18, 2007, vol. 35 No. 12, e87; 8 pages total.

Sautter, et al.; "Selection of High-Producing CHO Cells Using NPT Selection Marker With Reduced Enzyme Activity", Biotechnology and Bioengineering, Published Mar. 5, 2005, vol. 89 No. 5, pp. 530-538.

Chen, et al.; "Highly Efficient Selection of the Stable Clones Expressing Antibody-IL-2 Fusion Protein by a Dicistronic Expression Vector Containing a Mutant Neo Gene", Journal of Immunological Methods, Published Oct. 4, 2004, vol. 295, pp. 49-56.

Ng, et al.; "Application of Destabilizing Sequences on Selection Marker for Improved Recombinant Protein Productivity in CHO-DG44", Metabolic Engineering, Published Feb. 14, 2007, vol. 9, pp. 304-316.

Kim, et al.; "Codon Optimization for High-Level Expression of Human Erythropoietin (EPO) in Mammalian Cells", Gene, Published 1997, vol. 199, pp. 293-301.

International Searching Authority, International Search Report issued in PCT/JP2011/078938, dated Jan. 17, 2012.

Huang, Xin, et al., "Gene Transfer Efficiency and Genome-Wide Integration Profiling of Sleeping Beauty, Tol2, and PiggyBac Transposons in Human Primary T Cells," Molecular Therapy, Oct. 2010, vol. 18, No. 10, pp. 1803-1813.

Communication from the European Patent Office issued Jun. 26, 2015, in counterpart European Patent Application No. 11848634.9.

\* cited by examiner

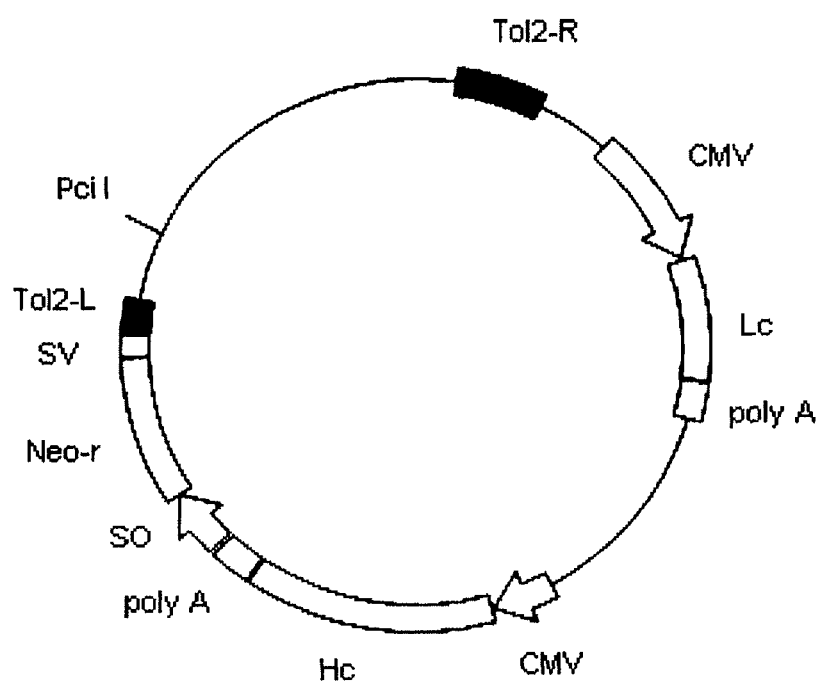

SEQUENCE LISTING

```
<160> NUMBER OF SEQ ID NOS: 37

<210> SEQ ID NO 1
<211> LENGTH: 2788
<212> TYPE: DNA
<213> ORGANISM: Artificial
<220> FEATURE:
<223> OTHER INFORMATION: Description of artificial sequence;
      nonautologus Tol2 transposon
```

```
<400> SEQUENCE: 1
cagaggtgta aagtacttga gtaattttac ttgattactg tacttaagta ttattttttgg      60 ggattttttac tttacttgag tacaattaaa aatcaatact tttactttta cttaattaca     120 ttttttttaga aaaaaagta cttttttactc cttacaattt tatttacagt caaaaagtac     180
ttattttttg gagatcactt cattctatttt tcccttgcta ttaccaaacc aattgaattg     240
cgctgatgcc cagtttaatt taaatgttat ttattctgcc tatgaaaatc gttttcacat     300
tatatgaaat tggtcagaca tgttcattgg tcctttggaa gtgacgtcat gtcacatcta     360
ttaccacaat gcacagcacc ttgacctgga aattagggaa attataacag tcaatcagtg     420
gaagaaaatg gaggaagtat gtgattcatc agcagctgcg agcagcacag tccaaaatca     480
gccacaggat caagagcacc cgtggccgta tcttcgcgaa ttcttttctt taagtggtgt     540
aaataaagat tcattcaaga tgaaatgtgt cctctgtctc ccgcttaata aagaaatatc     600
ggccttcaaa agttcgccat caaacctaag gaagcatatt gaggtaagta cattaagtat     660 tttgtttttac tgatagtttt tttttttttt tttttttttt tttttgggtg tgcatgtttt     720
gacgttgatg gcgcgccttt tatatgtgta gtaggcctat tttcactaat gcatgcgatt     780
gacaatataa ggctcacgta ataaaatgct aaaatgcatt tgtaattggt aacgttaggt     840
ccacgggaaa tttggcgcct attgcagctt tgaataatca ttatcattcc gtgctctcat     900 tgtgttttgaa ttcatgcaaa acacaagaaa accaagcgag aaatttttt ccaaacatgt     960 tgtattgtca aaacggtaac actttacaat gaggttgatt agttcatgta ttaactaaca    1020
ttaaataacc atgagcaata catttgttac tgtatctgtt aatctttgtt aacgttagtt    1080
aatagaaata cagatgttca ttgtttgttc atgttagttc acagtgcatt aactaatgtt    1140
aacaagatat aaagtattag taaatgttga aattaacatg tatacgtgca gttcattatt    1200
agttcatgtt aactaatgta gttaactaac gaaccttatt gtaaaagtgt taccatcaaa    1260
actaatgtaa tgaaatcaat tcaccctgtc atgtcagcct tacagtcctg tgttttttgtc    1320 aatataatca gaaataaaat taatgtttga ttgtcactaa atgctactgt atttctaaaa    1380
tcaacaagta tttaacatta taaagtgtgc aattggctgc aaatgtcagt tttattaaag    1440
ggttagttca cccaaaaatg aaaataatgt cattaatgac tcgccctcat gtcgttccaa    1500
gcccgtaaga cctccgttca tcttcagaac acagtttaag atattttaga tttagtccga    1560
gagctttctg tgcctccatt gagaatgtat gtacggtata ctgtccatgt ccagaaaggt    1620
aataaaaaca tcaaagtagt ccatgtgaca tcagtgggtt agttagaatt ttttgaagca    1680
tcgaatacat tttggtccaa aaataacaaa acctacgact ttattcggca ttgtattctc    1740
ttccgggtct gttgtcaatc cgcgttcacg acttcgcagt gacgctacaa tgctgaataa    1800
agtcgtaggt tttgttatt tggaccaaa atgtatttc gatgcttcaa ataattctac    1860
ctaacccact gatgtcacat ggactacttt gatgttttta ttaccttcct ggacatggac    1920
agtataccgt acatacattt tcagtggagg gacagaaagc tctcggacta aatctaaaat    1980
atcttaaact gtgttccgaa gatgaacgga ggtgttacgg gcttggaacg acatgagggt    2040
gagtcattaa tgcatctctt tcatttttgg gtgaactaac cctttaatgc tgtaatcaga    2100
gagtgtatgt gtaattgtta catttattgc atacaatata aatatttatt tgttgttttt    2160
acagagaatg cacccaaatt acctcaaaaa ctactctaaa ttgacagcac agaagagaaa    2220
gatcgggaca gatctcatat gctcgagggc ccatctggcc tgtgtttcag acaccaggga    2280
gtctctgctc acgttttcctg ctatttgcag cctctctatc aagactaata cacctcttcc    2340
```

```
cgcatcggct gcctgtgaga ggcttttcag cactgcagga ttgcttttca gccccaaaag    2400
agctaggctt gacactaaca attttgagaa tcagcttcta ctgaagttaa atctgaggtt    2460
ttacaacttt gagtagcgtg tactggcatt agattgtctg tcttatagtt tgataattaa    2520
atacaaacag ttctaaagca ggataaaacc ttgtatgcat ttcatttaat gttttttgag    2580
attaaaagct taaacaagaa tctctagttt tctttcttgc ttttactttt acttccttaa    2640
tactcaagta caattttaat ggagtacttt tttactttta ctcaagtaag attctagcca    2700
gatactttta cttttaattg agtaaaattt tccctaagta cttgtacttt cacttgagta    2760
aaatttttga gtacttttta cacctctg                                        2788

<210> SEQ ID NO 2
<211> LENGTH: 200
<212> TYPE: DNA
<213> ORGANISM: Artificial
<220> FEATURE:
<223> OTHER INFORMATION: Description of artificial sequence; Tol2-L
      transposon sequence

<400> SEQUENCE: 2
cagaggtgta aagtacttga gtaattttac ttgattactg tacttaagta ttatttttgg     60
ggatttttac tttacttgag tacaattaaa aatcaatact tttactttta cttaattaca    120

ttttttaga aaaaaagta ctttttactc cttacaattt tatttacagt caaaaagtac      180
ttattttttg gagatcactt                                                 200

<210> SEQ ID NO 3
<211> LENGTH: 504
<212> TYPE: DNA
<213> ORGANISM: Artificial
<220> FEATURE:
<223> OTHER INFORMATION: Description of artificial sequence; Tol2-R
      transposon sequence

<400> SEQUENCE: 3
ctgctcacgt ttcctgctat ttgcagcctc tctatcaaga ctaatacacc tcttcccgca     60
tcggctgcct gtgagaggct tttcagcact gcaggattgc ttttcagccc caaaagagct   120
aggcttgaca ctaacaattt tgagaatcag cttctactga agttaaatct gaggttttac   180
aactttgagt agcgtgtact ggcattagat tgtctgtctt atagtttgat aattaaatac   240
aaacagttct aaagcaggat aaaaccttgt atgcatttca tttaatgttt tttgagatta   300
aaagcttaaa caagaatctc tagttttctt tcttgctttt acтттtacттт ccttaatact   360 caagtacaat tttaatggag tacttttta cttttactca gtaagattc tagccagata     420 cttttacttt taattgagta aaattttccc taagtacttg tactttcact tgagtaaaat   480

tttgagtac tttttacacc tctg                                           504

<210> SEQ ID NO 4
<211> LENGTH: 2156
<212> TYPE: DNA
<213> ORGANISM: Oryzias latipes
<220> FEATURE:
<221> NAME/KEY: CDS
<222> LOCATION: (85)..(2034)

<400> SEQUENCE: 4
acgtcatgtc acatctatta ccacaatgca cagcaccttg acctggaaat tagggaaatt      60
ataacagtca atcagtggaa gaaa atg gag gaa gta tgt gat tca tca gca         111
```

```
                Met Glu Glu Val Cys Asp Ser Ser Ala
                 1               5 gct gcg agc agc aca gtc caa aat cag cca cag gat caa gag cac ccg    159
Ala Ala Ser Ser Thr Val Gln Asn Gln Pro Gln Asp Gln Glu His Pro
 10              15                  20                  25 tgg ccg tat ctt cgc gaa ttc ttt tct tta agt ggt gta aat aaa gat    207
Trp Pro Tyr Leu Arg Glu Phe Phe Ser Leu Ser Gly Val Asn Lys Asp
                 30                  35                  40 tca ttc aag atg aaa tgt gtc ctc tgt ctc ccg ctt aat aaa gaa ata    255
Ser Phe Lys Met Lys Cys Val Leu Cys Leu Pro Leu Asn Lys Glu Ile
                 45                  50                  55 tcg gcc ttc aaa agt tcg cca tca aac cta agg aag cat att gag aga    303
Ser Ala Phe Lys Ser Ser Pro Ser Asn Leu Arg Lys His Ile Glu Arg
             60                  65                  70 atg cac cca aat tac ctc aaa aac tac tct aaa ttg aca gca cag aag    351
Met His Pro Asn Tyr Leu Lys Asn Tyr Ser Lys Leu Thr Ala Gln Lys
             75                  80                  85 aga aag atc ggg acc tcc acc cat gct tcc agc agt aag caa ctg aaa    399
Arg Lys Ile Gly Thr Ser Thr His Ala Ser Ser Ser Lys Gln Leu Lys
 90              95                 100                 105 gtt gac tca gtt ttc cca gtc aaa cat gtg tct cca gtc act gtg aac    447
Val Asp Ser Val Phe Pro Val Lys His Val Ser Pro Val Thr Val Asn
                110                 115                 120 aaa gct ata tta agg tac atc att caa gga ctt cat cct ttc agc act    495
Lys Ala Ile Leu Arg Tyr Ile Ile Gln Gly Leu His Pro Phe Ser Thr
            125                 130                 135 gtt gat ctg cca tca ttt aaa gag ctg att agt aca ctg cag cct ggc    543
Val Asp Leu Pro Ser Phe Lys Glu Leu Ile Ser Thr Leu Gln Pro Gly
            140                 145                 150 att tct gtc att aca agg cct act tta cgc tcc aag ata gct gaa gct    591
Ile Ser Val Ile Thr Arg Pro Thr Leu Arg Ser Lys Ile Ala Glu Ala
            155                 160                 165 gct ctg atc atg aaa cag aaa gtg act gct gcc atg agt gaa gtt gaa    639
Ala Leu Ile Met Lys Gln Lys Val Thr Ala Ala Met Ser Glu Val Glu
170                 175                 180                 185 tgg att gca acc aca acg gat tgt tgg act gca cgt aga aag tca ttc    687
Trp Ile Ala Thr Thr Thr Asp Cys Trp Thr Ala Arg Arg Lys Ser Phe
                190                 195                 200 att ggt gta act gct cac tgg atc aac cct gga agt ctt gaa aga cat    735
Ile Gly Val Thr Ala His Trp Ile Asn Pro Gly Ser Leu Glu Arg His
                205                 210                 215 tcc gct gca ctt gcc tgc aaa aga tta atg ggc tct cat act ttt gag    783
Ser Ala Ala Leu Ala Cys Lys Arg Leu Met Gly Ser His Thr Phe Glu
            220                 225                 230 gta ctg gcc agt gcc atg aat gat atc cac tca gag tat gaa ata cgt    831
Val Leu Ala Ser Ala Met Asn Asp Ile His Ser Glu Tyr Glu Ile Arg
235                 240                 245 gac aag gtt gtt tgc aca acc aca gac agt ggt tcc aac ttt atg aag    879
Asp Lys Val Val Cys Thr Thr Thr Asp Ser Gly Ser Asn Phe Met Lys
250                 255                 260                 265 gct ttc aga gtt ttt ggt gtg gaa aac aat gat atc gag act gag gca    927
Ala Phe Arg Val Phe Gly Val Glu Asn Asn Asp Ile Glu Thr Glu Ala
                270                 275                 280 aga agg tgt gaa agt gat gac act gat tct gaa ggc tgt ggt gag gga    975
Arg Arg Cys Glu Ser Asp Asp Thr Asp Ser Glu Gly Cys Gly Glu Gly
            285                 290                 295 agt gat ggt gtg gaa ttc caa gat gcc tca cga gtc ctg gac caa gac   1023
Ser Asp Gly Val Glu Phe Gln Asp Ala Ser Arg Val Leu Asp Gln Asp
            300                 305                 310
```

```
gat ggc ttc gaa ttc cag cta cca aaa cat caa aag tgt gcc tgt cac   1071
Asp Gly Phe Glu Phe Gln Leu Pro Lys His Gln Lys Cys Ala Cys His
315                 320                 325 tta ctt aac cta gtc tca agc gtt gat gcc caa aaa gct ctc tca aat   1119
Leu Leu Asn Leu Val Ser Ser Val Asp Ala Gln Lys Ala Leu Ser Asn
330                 335                 340                 345 gaa cac tac aag aaa ctc tac aga tct gtc ttt ggc aaa tgc caa gct   1167
Glu His Tyr Lys Lys Leu Tyr Arg Ser Val Phe Gly Lys Cys Gln Ala
                350                 355                 360 tta tgg aat aaa agc agc cga tcg gct cta gca gct gaa gct gtt gaa   1215
Leu Trp Asn Lys Ser Ser Arg Ser Ala Leu Ala Ala Glu Ala Val Glu
        365                 370                 375 tca gaa agc cgg ctt cag ctt tta agg cca aac caa acg cgg tgg aat   1263
Ser Glu Ser Arg Leu Gln Leu Leu Arg Pro Asn Gln Thr Arg Trp Asn
            380                 385                 390 tca act ttt atg gct gtt gac aga att ctt caa att tgc aaa gaa gca   1311
Ser Thr Phe Met Ala Val Asp Arg Ile Leu Gln Ile Cys Lys Glu Ala
395                 400                 405 gga gaa ggc gca ctt cgg aat ata tgc acc tct ctt gag gtt cca atg   1359
Gly Glu Gly Ala Leu Arg Asn Ile Cys Thr Ser Leu Glu Val Pro Met
410                 415                 420                 425 ttt aat cca gca gaa atg ctg ttc ttg aca gag tgg gcc aac aca atg   1407
Phe Asn Pro Ala Glu Met Leu Phe Leu Thr Glu Trp Ala Asn Thr Met
                430                 435                 440 cgt cca gtt gca aaa gta ctc gac atc ttg caa gcg gaa acg aat aca   1455
Arg Pro Val Ala Lys Val Leu Asp Ile Leu Gln Ala Glu Thr Asn Thr
        445                 450                 455 cag ctg ggg tgg ctg ctg cct agt gtc cat cag tta agc ttg aaa ctt   1503
Gln Leu Gly Trp Leu Leu Pro Ser Val His Gln Leu Ser Leu Lys Leu
            460                 465                 470 cag cga ctc cac cat tct ctc agg tac tgt gac cca ctt gtg gat gcc   1551
Gln Arg Leu His His Ser Leu Arg Tyr Cys Asp Pro Leu Val Asp Ala
475                 480                 485 cta caa caa gga atc caa aca cga ttc aag cat atg ttt gaa gat cct   1599
Leu Gln Gln Gly Ile Gln Thr Arg Phe Lys His Met Phe Glu Asp Pro
490                 495                 500                 505 gag atc ata gca gct gcc atc ctt ctc cct aaa ttt cgg acc tct tgg   1647
Glu Ile Ile Ala Ala Ala Ile Leu Leu Pro Lys Phe Arg Thr Ser Trp
                510                 515                 520 aca aat gat gaa acc atc ata aaa cga ggc atg gac tac atc aga gtg   1695
Thr Asn Asp Glu Thr Ile Ile Lys Arg Gly Met Asp Tyr Ile Arg Val
        525                 530                 535 cat ctg gag cct ttg gac cac aag aag gaa ttg gcc aac agt tca tct   1743
His Leu Glu Pro Leu Asp His Lys Lys Glu Leu Ala Asn Ser Ser Ser
            540                 545                 550 gat gat gaa gat ttt ttc gct tct ttg aaa ccg aca aca cat gaa gcc   1791
Asp Asp Glu Asp Phe Phe Ala Ser Leu Lys Pro Thr Thr His Glu Ala
555                 560                 565 agc aaa gag ttg gat gga tat ctg gcc tgt gtt tca gac acc agg gag   1839
Ser Lys Glu Leu Asp Gly Tyr Leu Ala Cys Val Ser Asp Thr Arg Glu
570                 575                 580                 585 tct ctg ctc acg ttt cct gct att tgc agc ctc tct atc aag act aat   1887
Ser Leu Leu Thr Phe Pro Ala Ile Cys Ser Leu Ser Ile Lys Thr Asn
                590                 595                 600 aca cct ctt ccc gca tcg gct gcc tgt gag agg ctt ttc agc act gca   1935
Thr Pro Leu Pro Ala Ser Ala Ala Cys Glu Arg Leu Phe Ser Thr Ala
        605                 610                 615 gga ttg ctt ttc agc ccc aaa aga gct agg ctt gac act aac aat ttt   1983
Gly Leu Leu Phe Ser Pro Lys Arg Ala Arg Leu Asp Thr Asn Asn Phe
            620                 625                 630
```

-continued

```
gag aat cag ctt cta ctg aag tta aat ctg agg ttt tac aac ttt gag    2031
Glu Asn Gln Leu Leu Leu Lys Leu Asn Leu Arg Phe Tyr Asn Phe Glu
    635                 640                 645 tag cgtgtactgg cattagattg tctgtcttat agtttgataa ttaaatacaa         2084
acagttctaa agcaggataa aaccttgtat gcatttcatt taatgttttt tgagattaaa  2144
agcttaaaca ag                                                      2156

<210> SEQ ID NO 5
<211> LENGTH: 649
<212> TYPE: PRT
<213> ORGANISM: Oryzias latipes

<400> SEQUENCE: 5

Met Glu Glu Val Cys Asp Ser Ser Ala Ala Ser Ser Thr Val Gln
1               5                   10                  15

Asn Gln Pro Gln Asp Gln Glu His Pro Trp Pro Tyr Leu Arg Glu Phe
            20                  25                  30

Phe Ser Leu Ser Gly Val Asn Lys Asp Ser Phe Lys Met Lys Cys Val
        35                  40                  45

Leu Cys Leu Pro Leu Asn Lys Glu Ile Ser Ala Phe Lys Ser Ser Pro
    50                  55                  60

Ser Asn Leu Arg Lys His Ile Glu Arg Met His Pro Asn Tyr Leu Lys
65                  70                  75                  80

Asn Tyr Ser Lys Leu Thr Ala Gln Lys Arg Lys Ile Gly Thr Ser Thr
                85                  90                  95

His Ala Ser Ser Lys Gln Leu Lys Val Asp Ser Val Phe Pro Val
            100                 105                 110

Lys His Val Ser Pro Val Thr Val Asn Lys Ala Ile Leu Arg Tyr Ile
        115                 120                 125

Ile Gln Gly Leu His Pro Phe Ser Thr Val Asp Leu Pro Ser Phe Lys
    130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Ala Leu Ile Met Lys Gln Lys
                165                 170                 175

Val Thr Ala Ala Met Ser Glu Val Glu Trp Ile Ala Thr Thr Asp
            180                 185                 190

Cys Trp Thr Ala Arg Arg Lys Ser Phe Ile Gly Val Thr Ala His Trp
        195                 200                 205

Ile Asn Pro Gly Ser Leu Glu Arg His Ser Ala Ala Leu Ala Cys Lys
    210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
                245                 250                 255

Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285

Thr Asp Ser Glu Gly Cys Gly Glu Gly Ser Asp Gly Val Glu Phe Gln
    290                 295                 300

Asp Ala Ser Arg Val Leu Asp Gln Asp Asp Gly Phe Glu Phe Gln Leu
305                 310                 315                 320
```

```
Pro Lys His Gln Lys Cys Ala Cys His Leu Leu Asn Leu Val Ser Ser
                325                 330                 335

Val Asp Ala Gln Lys Ala Leu Ser Asn Glu His Tyr Lys Lys Leu Tyr
            340                 345                 350

Arg Ser Val Phe Gly Lys Cys Gln Ala Leu Trp Asn Lys Ser Ser Arg
        355                 360                 365

Ser Ala Leu Ala Ala Glu Ala Val Glu Ser Glu Ser Arg Leu Gln Leu
    370                 375                 380

Leu Arg Pro Asn Gln Thr Arg Trp Asn Ser Thr Phe Met Ala Val Asp
385                 390                 395                 400

Arg Ile Leu Gln Ile Cys Lys Glu Ala Gly Glu Gly Ala Leu Arg Asn
                405                 410                 415

Ile Cys Thr Ser Leu Glu Val Pro Met Phe Asn Pro Ala Glu Met Leu
            420                 425                 430

Phe Leu Thr Glu Trp Ala Asn Thr Met Arg Pro Val Ala Lys Val Leu
        435                 440                 445

Asp Ile Leu Gln Ala Glu Thr Asn Thr Gln Leu Gly Trp Leu Leu Pro
    450                 455                 460

Ser Val His Gln Leu Ser Leu Lys Leu Gln Arg Leu His His Ser Leu
465                 470                 475                 480

Arg Tyr Cys Asp Pro Leu Val Asp Ala Leu Gln Gln Gly Ile Gln Thr
                485                 490                 495

Arg Phe Lys His Met Phe Glu Asp Pro Glu Ile Ile Ala Ala Ala Ile
            500                 505                 510

Leu Leu Pro Lys Phe Arg Thr Ser Trp Thr Asn Asp Glu Thr Ile Ile
        515                 520                 525

Lys Arg Gly Met Asp Tyr Ile Arg Val His Leu Glu Pro Leu Asp His
    530                 535                 540

Lys Lys Glu Leu Ala Asn Ser Ser Ser Asp Asp Glu Asp Phe Phe Ala
545                 550                 555                 560

Ser Leu Lys Pro Thr Thr His Glu Ala Ser Lys Glu Leu Asp Gly Tyr
                565                 570                 575

Leu Ala Cys Val Ser Asp Thr Arg Glu Ser Leu Leu Thr Phe Pro Ala
            580                 585                 590

Ile Cys Ser Leu Ser Ile Lys Thr Asn Thr Pro Leu Pro Ala Ser Ala
        595                 600                 605

Ala Cys Glu Arg Leu Phe Ser Thr Ala Gly Leu Leu Phe Ser Pro Lys
    610                 615                 620

Arg Ala Arg Leu Asp Thr Asn Asn Phe Glu Asn Gln Leu Leu Leu Lys
625                 630                 635                 640

Leu Asn Leu Arg Phe Tyr Asn Phe Glu
                645

<210> SEQ ID NO 6
<211> LENGTH: 4682
<212> TYPE: DNA
<213> ORGANISM: Oryzias latipes

<400> SEQUENCE: 6
cagaggtgta aagtacttga gtaattttac ttgattactg tacttaagta ttattttttgg      60 ggattttttac tttacttgag tacaattaaa aatcaatact tttactttta cttaattaca     120 ttttttttaga aaaaaaagta cttttttactc cttacaattt tatttacagt caaaaagtac    180 ttatttttttg gagatcactt cattctattt tcccttgcta ttaccaaacc aattgaattg     240
```

-continued

```
cgctgatgcc cagtttaatt taaatgttat ttattctgcc tatgaaaatc gttttcacat    300
tatatgaaat tggtcagaca tgttcattgg tcctttggaa gtgacgtcat gtcacatcta    360
ttaccacaat gcacagcacc ttgacctgga aattagggaa attataacag tcaatcagtg    420
gaagaaaatg gaggaagtat gtgattcatc agcagctgcg agcagcacag tccaaaatca    480
gccacaggat caagagcacc cgtggccgta tcttcgcgaa ttcttttctt taagtggtgt    540
aaataaagat tcattcaaga tgaaatgtgt cctctgtctc ccgcttaata agaaatatc     600 ggccttcaaa agttcgccat caaacctaag gaagcatatt gaggtaagta cattaagtat    660
tttgttttac tgatagtttt tttttttttt tttttttttt tttttgggtg tgcatgtttt    720
gacgttgatg gcgcgccttt tatatgtgta gtaggcctat tttcactaat gcatgcgatt    780
gacaatataa ggctcacgta ataaaatgct aaaatgcatt tgtaattggt aacgttaggt    840
ccacgggaaa tttggcgcct attgcagctt tgaataatca ttatcattcc gtgctctcat    900
tgtgtttgaa ttcatgcaaa acacaagaaa accaagcgag aaattttttt ccaaacatgt    960
tgtattgtca aaacggtaac actttacaat gaggttgatt agttcatgta ttaactaaca    1020
ttaaataacc atgagcaata catttgttac tgtatctgtt aatctttgtt aacgttagtt    1080
aatagaaata cagatgttca ttgtttgttc atgttagttc acagtgcatt aactaatgtt    1140
aacaagatat aaagtattag taaatgttga aattaacatg tatacgtgca gttcattatt    1200
agttcatgtt aactaatgta gttaactaac gaaccttatt gtaaaagtgt taccatcaaa    1260
actaatgtaa tgaaatcaat tcaccctgtc atgtcagcct tacagtcctg tgttttttgtc   1320 aatataatca gaaataaaat taatgtttga ttgtcactaa atgctactgt atttctaaaa    1380
tcaacaagta tttaacatta taaagtgtgc aattggctgc aaatgtcagt tttattaaag    1440
ggttagttca cccaaaaatg aaaataatgt cattaatgac tcgccctcat gtcgttccaa    1500
gcccgtaaga cctccgttca tcttcagaac acagtttaag atattttaga tttagtccga    1560
gagctttctg tgcctccatt gagaatgtat gtacggtata ctgtccatgt ccagaaaggt    1620
aataaaaaca tcaaagtagt ccatgtgaca tcagtgggtt agttagaatt ttttgaagca    1680
tcgaatacat tttggtccaa aaataacaaa acctacgact ttattcggca ttgtattctc    1740
ttccgggtct gttgtcaatc cgcgttcacg acttcgcagt gacgctacaa tgctgaataa    1800
agtcgtaggt tttgttattt ttggaccaaa atgtattttc gatgcttcaa ataattctac    1860
ctaacccact gatgtcacat ggactacttt gatgttttta ttacctttct ggacatggac    1920
agtataccgt acatacattt tcagtggagg gacagaaagc tctcggacta aatctaaaat    1980
atcttaaact gtgttccgaa gatgaacgga ggtgttacgg gcttggaacg acatgagggt    2040
gagtcattaa tgcatctttt tcatttttgg gtgaactaac cctttaatgc tgtaatcaga    2100
gagtgtatgt gtaattgtta catttattgc atacaatata aatatttatt tgttgttttt    2160
acagagaatg cacccaaatt acctcaaaaa ctactctaaa ttgacagcac agaagagaaa    2220
gatcgggacc tccacccatg cttccagcag taagcaactg aaagttgact cagttttccc    2280
agtcaaacat gtgtctccag tcactgtgaa caaagctata ttaaggtaca tcattcaagg    2340
acttcatcct ttcagcactg ttgatctgcc atcatttaaa gagctgatta gtacactgca    2400
gcctggcatt tctgtcatta caaggcctac tttacgctcc aagatagctg aagctgctct    2460
gatcatgaaa cagaaagtga ctgctgccat gagtgaagtt gaatggattg caaccacaac    2520
ggattgttgg actgcacgta gaaagtcatt cattggtgta actgctcact ggatcaaccc    2580
tggaagtctt gaaagacatt ccgctgcact tgcctgcaaa agattaatgg gctctcatac    2640
```

```
ttttgaggta ctggccagtg ccatgaatga tatccactca gagtatgaaa tacgtgacaa   2700
ggttgtttgc acaaccacag acagtggttc aactttatg aaggctttca gagttttgg    2760 tgtggaaaac aatgatatcg agactgaggc aagaaggtgt gaaagtgatg acactgattc   2820
tgaaggctgt ggtgagggaa gtgatggtgt ggaattccaa gatgcctcac gagtcctgga   2880
ccaagacgat ggcttcgaat tccagctacc aaaacatcaa agtgtgcct  gtcacttact   2940 taacctagtc tcaagcgttg atgcccaaaa agctctctca aatgaacact acaagaaact   3000
ctacagatct gtctttggca atgccaagc tttatggaat aaaagcagcc gatcggctct    3060
agcagctgaa gctgttgaat cagaaagccg cttcagctt taaggccaa accaaacgcg     3120 gtggaattca acttttatgg ctgttgacag aattcttcaa atttgcaaag aagcaggaga   3180
aggcgcactt cggaatatat gcacctctct tgaggttcca atgtaagtgt ttttcccctc   3240
tatcgatgta acaaatgtg ggttgttttt gtttaatact ctttgattat gctgatttct    3300
cctgtaggtt taatccagca gaaatgctgt tcttgacaga gtgggccaac acaatgcgtc   3360
cagttgcaaa agtactcgac atcttgcaag cggaaacgaa tacacagctg ggtggctgc    3420 tgcctagtgt ccatcagtta agcttgaaac ttcagcgact ccaccattct ctcaggtact   3480
gtgacccact tgtggatgcc ctacaacaag gaatccaaac acgattcaag catatgtttg   3540
aagatcctga gatcatagca gctgccatcc ttctccctaa atttcggacc tcttggacaa   3600
atgatgaaac catcataaaa cgaggtaaat gaatgcaagc aacatacact tgacgaattc   3660
taatctgggc aacctttgag ccataccaaa attattcttt tatttattta tttttgcact   3720
ttttaggaat gttatatccc atctttggct gtgatctcaa tatgaatatt gatgtaaagt   3780
attcttgcag caggttgtag ttatccctca gtgtttcttg aaaccaaact catatgtatc   3840
atatgtggtt tggaaatgca gttagatttt atgctaaaat aagggatttg catgatttta   3900
gatgtagatg actgcacgta aatgtagtta atgacaaaat ccataaaatt tgttcccagt   3960
cagaagcccc tcaaccaaac ttttctttgt gtctgctcac tgtgcttgta ggcatggact   4020
acatcagagt gcatctggag cctttggacc acaagaagga attggccaac agttcatctg   4080
atgatgaaga ttttttcgct tctttgaaac cgacaacaca tgaagccagc aaagagttgg   4140
atggatatct ggcctgtgtt tcagacacca gggagtctct gctcacgttt cctgctatt    4200 gcagcctctc tatcaagact aatacacctc ttcccgcatc ggctgccgt  gagaggcttt    4260 tcagcactgc aggattgctt ttcagcccca aaagagctag gcttgacact aacaattttg   4320
agaatcagct tctactgaag ttaaatctga ggttttacaa ctttgagtag cgtgtactgg   4380
cattagattg tctgtcttat agtttgataa ttaaatacaa acagttctaa agcaggataa   4440
aaccttgtat gcatttcatt taatgttttt tgagattaaa agcttaaaca agaatctcta   4500
gttttctttc ttgcttttac ttttacttcc ttaatactca agtacaattt taatggagta   4560
cttttttact tttactcaag taagattcta gccagatact tttactttta attgagtaaa   4620
attttcccta agtacttgta ctttcacttg agtaaaattt ttgagtactt tttacacctc   4680
tg                                                                  4682
```

<210> SEQ ID NO 7
<211> LENGTH: 795
<212> TYPE: DNA
<213> ORGANISM: unknown
<220> FEATURE:
<223> OTHER INFORMATION: wild type neomycin resistant gene
<220> FEATURE:

<221> NAME/KEY: CDS
<222> LOCATION: (1)..(795)

<400> SEQUENCE: 7

```
atg att gaa caa gat gga ttg cac gca ggt tct ccg gcc gct tgg gtg      48
Met Ile Glu Gln Asp Gly Leu His Ala Gly Ser Pro Ala Ala Trp Val
1               5                   10                  15 gag agg cta ttc ggc tat gac tgg gca caa cag aca atc ggc tgc tct      96
Glu Arg Leu Phe Gly Tyr Asp Trp Ala Gln Gln Thr Ile Gly Cys Ser
            20                  25                  30 gat gcc gcc gtg ttc cgg ctg tca gcg cag ggg cgc ccg gtt ctt ttt     144
Asp Ala Ala Val Phe Arg Leu Ser Ala Gln Gly Arg Pro Val Leu Phe
        35                  40                  45 gtc aag acc gac ctg tcc ggt gcc ctg aat gaa ctg cag gac gag gca     192
Val Lys Thr Asp Leu Ser Gly Ala Leu Asn Glu Leu Gln Asp Glu Ala
    50                  55                  60 gcg cgg cta tcg tgg ctg gcc acg acg ggc gtt cct tgc gca gct gtg     240
Ala Arg Leu Ser Trp Leu Ala Thr Thr Gly Val Pro Cys Ala Ala Val
65                  70                  75                  80 ctc gac gtt gtc act gaa gcg gga agg gac tgg ctg cta ttg ggc gaa     288
Leu Asp Val Val Thr Glu Ala Gly Arg Asp Trp Leu Leu Leu Gly Glu
                85                  90                  95 gtg ccg ggg cag gat ctc ctg tca tct cac ctt gct cct gcc gag aaa     336
Val Pro Gly Gln Asp Leu Leu Ser Ser His Leu Ala Pro Ala Glu Lys
            100                 105                 110 gta tcc atc atg gct gat gca atg cgg cgg ctg cat acg ctt gat ccg     384
Val Ser Ile Met Ala Asp Ala Met Arg Arg Leu His Thr Leu Asp Pro
        115                 120                 125 gct acc tgc cca ttc gac cac caa gcg aaa cat cgc atc gag cga gca     432
Ala Thr Cys Pro Phe Asp His Gln Ala Lys His Arg Ile Glu Arg Ala
    130                 135                 140 cgt act cgg atg gaa gcc ggt ctt gtc gat cag gat gat ctg gac gaa     480
Arg Thr Arg Met Glu Ala Gly Leu Val Asp Gln Asp Asp Leu Asp Glu
145                 150                 155                 160 gag cat cag ggg ctc gcg cca gcc gaa ctg ttc gcc agg ctc aag gcg     528
Glu His Gln Gly Leu Ala Pro Ala Glu Leu Phe Ala Arg Leu Lys Ala
                165                 170                 175 cgc atg ccc gac ggc gag gat ctc gtc gtg acc cat ggc gat gcc tgc     576
Arg Met Pro Asp Gly Glu Asp Leu Val Val Thr His Gly Asp Ala Cys
            180                 185                 190 ttg ccg aat atc atg gtg gaa aat ggc cgc ttt tct gga ttc atc gac     624
Leu Pro Asn Ile Met Val Glu Asn Gly Arg Phe Ser Gly Phe Ile Asp
        195                 200                 205 tgt ggc cgg ctg ggt gtg gcg gac cgc tat cag gac ata gcg ttg gct     672
Cys Gly Arg Leu Gly Val Ala Asp Arg Tyr Gln Asp Ile Ala Leu Ala
    210                 215                 220 acc cgt gat att gct gaa gag ctt ggc ggc gaa tgg gct gac cgc ttc     720
Thr Arg Asp Ile Ala Glu Glu Leu Gly Gly Glu Trp Ala Asp Arg Phe
225                 230                 235                 240 ctc gtg ctt tac ggt atc gcc gct ccc gat tcg cag cgc atc gcc ttc     768
Leu Val Leu Tyr Gly Ile Ala Ala Pro Asp Ser Gln Arg Ile Ala Phe
                245                 250                 255 tat cgc ctt ctt gac gag ttc ttc tga                                 795
Tyr Arg Leu Leu Asp Glu Phe Phe
            260
```

<210> SEQ ID NO 8
<211> LENGTH: 264
<212> TYPE: PRT
<213> ORGANISM: unknown
<220> FEATURE:

<223> OTHER INFORMATION: Synthetic Construct

<400> SEQUENCE: 8

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 9
<211> LENGTH: 795
<212> TYPE: DNA
<213> ORGANISM: Artificial
<220> FEATURE:
<223> OTHER INFORMATION: modified neomycin resistant gene
<220> FEATURE:
<221> NAME/KEY: CDS
<222> LOCATION: (1)..(795)

<400> SEQUENCE: 9

```
atg att gaa caa gat gga ttg cac gca ggt tct ccg gcc gct tgg gtg      48
Met Ile Glu Gln Asp Gly Leu His Ala Gly Ser Pro Ala Ala Trp Val
1               5                   10                  15 gag agg cta ttc ggc tat gac tgg gca caa cag aca atc ggc tgc tct      96
Glu Arg Leu Phe Gly Tyr Asp Trp Ala Gln Gln Thr Ile Gly Cys Ser
            20                  25                  30 gat gcc gcc gtg ttc cgg ctg tca gcg cag ggg cgc ccg gtt ctt ttt     144
Asp Ala Ala Val Phe Arg Leu Ser Ala Gln Gly Arg Pro Val Leu Phe
        35                  40                  45
```

```
gtc aag acc gac ctg tcc ggt gcc ctg aat gaa ctg caa gat gaa gcg    192
Val Lys Thr Asp Leu Ser Gly Ala Leu Asn Glu Leu Gln Asp Glu Ala
 50              55                  60 gcg cga tta tcg tgg tta gcg acg acg ggg gta ccg tgt gcg gcg gta    240
Ala Arg Leu Ser Trp Leu Ala Thr Thr Gly Val Pro Cys Ala Ala Val
 65              70                  75                  80 tta gat gta gta acg gaa gcg ggg cga gat tgg tta tta ggg gaa        288
Leu Asp Val Val Thr Glu Ala Gly Arg Asp Trp Leu Leu Gly Glu
                 85                  90                  95 gta ccg ggg caa gat tta tta tcg tcg cat tta gcg ccg gcg gaa aaa    336
Val Pro Gly Gln Asp Leu Leu Ser Ser His Leu Ala Pro Ala Glu Lys
            100                 105                 110 gta tcg ata atg gcg gat gcg atg cga cga tta cat acg tta gat ccg    384
Val Ser Ile Met Ala Asp Ala Met Arg Arg Leu His Thr Leu Asp Pro
            115                 120                 125 gcg acg tgt ccg ttt gat cat caa gcg aaa cat cga ata gaa cga gcg    432
Ala Thr Cys Pro Phe Asp His Gln Ala Lys His Arg Ile Glu Arg Ala
130                 135                 140 cga acg cga atg gaa gcg ggg tta gta gat caa gat gat tta gat gaa    480
Arg Thr Arg Met Glu Ala Gly Leu Val Asp Gln Asp Asp Leu Asp Glu
145                 150                 155                 160 gaa cat caa ggg tta gcg ccg gcg gaa tta ttt gcg cga tta aaa gcg    528
Glu His Gln Gly Leu Ala Pro Ala Glu Leu Phe Ala Arg Leu Lys Ala
                165                 170                 175 cga atg ccg gat ggg gaa gat tta gta gta acg cat ggg gat gcg tgt    576
Arg Met Pro Asp Gly Glu Asp Leu Val Val Thr His Gly Asp Ala Cys
            180                 185                 190 tta ccg aat ata atg gta gaa aat ggg cga ttt tcg ggg ttt ata gat    624
Leu Pro Asn Ile Met Val Glu Asn Gly Arg Phe Ser Gly Phe Ile Asp
            195                 200                 205 tgt ggg cga tta ggg gta gcg gat cgt tat caa gat ata gcg tta gcg    672
Cys Gly Arg Leu Gly Val Ala Asp Arg Tyr Gln Asp Ile Ala Leu Ala
210                 215                 220 acg cga gat ata gcg gaa gaa tta ggg ggg gaa tgg gcg gat cga ttt    720
Thr Arg Asp Ile Ala Glu Glu Leu Gly Gly Glu Trp Ala Asp Arg Phe
225                 230                 235                 240 tta gta tta tat ggg ata gcg gcg ccg gat tcg caa cga ata gcg ttt    768
Leu Val Leu Tyr Gly Ile Ala Ala Pro Asp Ser Gln Arg Ile Ala Phe
                245                 250                 255 tat cga tta tta gat gaa ttt ttt tga                                795
Tyr Arg Leu Leu Asp Glu Phe Phe
            260

<210> SEQ ID NO 10
<211> LENGTH: 264
<212> TYPE: PRT
<213> ORGANISM: Artificial
<220> FEATURE:
<223> OTHER INFORMATION: Synthetic Construct

<400> SEQUENCE: 10

Met Ile Glu Gln Asp Gly Leu His Ala Gly Ser Pro Ala Ala Trp Val
 1               5                  10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
 50              55                  60
```

```
Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Leu Gly Glu
                 85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
210                 215                 220

Thr Arg Asp Ile Ala Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 11
<211> LENGTH: 795
<212> TYPE: DNA
<213> ORGANISM: artificial
<220> FEATURE:
<223> OTHER INFORMATION: modified neomycin resistant gene
<220> FEATURE:
<221> NAME/KEY: CDS
<222> LOCATION: (1)..(795)

<400> SEQUENCE: 11 atg att gaa caa gat gga ttg cac gca ggt tct ccg gcc gct tgg gtg      48
Met Ile Glu Gln Asp Gly Leu His Ala Gly Ser Pro Ala Ala Trp Val
 1               5                  10                  15 gag agg cta ttc ggc tat gac tgg gca caa cag aca atc ggc tgc tct     96
Glu Arg Leu Phe Gly Tyr Asp Trp Ala Gln Gln Thr Ile Gly Cys Ser
                 20                  25                  30 gat gcc gcc gtg ttc cgg ctg tca gcg cag ggg cgc ccg gtt ctt ttt    144
Asp Ala Ala Val Phe Arg Leu Ser Ala Gln Gly Arg Pro Val Leu Phe
             35                  40                  45 gta aaa acg gat tta tcg ggg gcg tta aat gaa tta caa gat gaa gcg    192
Val Lys Thr Asp Leu Ser Gly Ala Leu Asn Glu Leu Gln Asp Glu Ala
         50                  55                  60 gcg cga tta tcg tgg tta gcg acg acg ggg gta ccg tgt gcg gcg gta    240
Ala Arg Leu Ser Trp Leu Ala Thr Thr Gly Val Pro Cys Ala Ala Val
 65                  70                  75                  80 tta gat gta gta acg gaa gcg ggg cga gat tgg tta tta ttg ggg gaa    288
Leu Asp Val Val Thr Glu Ala Gly Arg Asp Trp Leu Leu Leu Gly Glu
                 85                  90                  95 gta ccg ggg caa gat tta tta tcg tcg cat tta gcg ccg gcg gaa aaa    336
Val Pro Gly Gln Asp Leu Leu Ser Ser His Leu Ala Pro Ala Glu Lys
            100                 105                 110
```

```
gta tcg ata atg gcg gat gcg atg cga cga tta cat acg tta gat ccg      384
Val Ser Ile Met Ala Asp Ala Met Arg Arg Leu His Thr Leu Asp Pro
        115                 120                 125 gcg acg tgt ccg ttt gat cat caa gcg aaa cat cga ata gaa cga gcg      432
Ala Thr Cys Pro Phe Asp His Gln Ala Lys His Arg Ile Glu Arg Ala
    130                 135                 140 cga acg cga atg gaa gcg ggg tta gta gat caa gat gat tta gat gaa      480
Arg Thr Arg Met Glu Ala Gly Leu Val Asp Gln Asp Asp Leu Asp Glu
145                 150                 155                 160 gaa cat caa ggg tta gcg ccg gcg gaa tta ttt gcg cga tta aaa gcg      528
Glu His Gln Gly Leu Ala Pro Ala Glu Leu Phe Ala Arg Leu Lys Ala
                165                 170                 175 cga atg ccg gat ggg gaa gat tta gta gta acg cat ggg gat gcg tgt      576
Arg Met Pro Asp Gly Glu Asp Leu Val Val Thr His Gly Asp Ala Cys
            180                 185                 190 tta ccg aat ata atg gta gaa aat ggg cga ttt tcg ggg ttt ata gat      624
Leu Pro Asn Ile Met Val Glu Asn Gly Arg Phe Ser Gly Phe Ile Asp
        195                 200                 205 tgt ggg cga tta ggg gta gcg gat cgt tat caa gat ata gcg tta gcg      672
Cys Gly Arg Leu Gly Val Ala Asp Arg Tyr Gln Asp Ile Ala Leu Ala
    210                 215                 220 acg cga gat ata gcg gaa gaa tta ggg ggg gaa tgg gcg gat cga ttt      720
Thr Arg Asp Ile Ala Glu Glu Leu Gly Gly Glu Trp Ala Asp Arg Phe
225                 230                 235                 240 tta gta tta tat ggg ata gcg gcg ccg gat tcg caa cga ata gcg ttt      768
Leu Val Leu Tyr Gly Ile Ala Ala Pro Asp Ser Gln Arg Ile Ala Phe
                245                 250                 255 tat cga tta tta gat gaa ttt ttt tga                                  795
Tyr Arg Leu Leu Asp Glu Phe Phe
            260

<210> SEQ ID NO 12
<211> LENGTH: 264
<212> TYPE: PRT
<213> ORGANISM: artificial
<220> FEATURE:
<223> OTHER INFORMATION: Synthetic Construct

<400> SEQUENCE: 12

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
        50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Gly Glu
                85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
        130                 135                 140

Arg Thr Arg Met Glu Ala Gly Leu Val Asp Gln Asp Asp Leu Asp Glu
```

|     |     |     |     |     |     |     |     |     |     |     |     |     |     |     |     |
| --- | --- | --- | --- | --- | --- | --- | --- | --- | --- | --- | --- | --- | --- | --- | --- |
| 145 |     |     |     | 150 |     |     |     | 155 |     |     |     | 160 |     |     |     |

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
                180                 185                 190

Leu Pro Asn Ile Met Val Glu Asn Gly Arg Phe Ser Gly Phe Ile Asp
                195                 200                 205

Cys Gly Arg Leu Gly Val Ala Asp Arg Tyr Gln Asp Ile Ala Leu Ala
                210                 215                 220

Thr Arg Asp Ile Ala Glu Glu Leu Gly Gly Glu Trp Ala Asp Arg Phe
225                   230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
                260

```
<210> SEQ ID NO 13
<211> LENGTH: 795
<212> TYPE: DNA
<213> ORGANISM: artificial
<220> FEATURE:
<223> OTHER INFORMATION: modified neomycin resistant gene
<220> FEATURE:
<221> NAME/KEY: CDS
<222> LOCATION: (1)..(795)

<400> SEQUENCE: 13
```

| | | | | | | | | | | | | | | | | |
|---|---|---|---|---|---|---|---|---|---|---|---|---|---|---|---|---|
| atg | att | gaa | caa | gat | gga | ttg | cac | gca | ggt | tct | ccg | gcc | gct | tgg | gtg | 48 |
| Met | Ile | Glu | Gln | Asp | Gly | Leu | His | Ala | Gly | Ser | Pro | Ala | Ala | Trp | Val | |
| 1 | | | | 5 | | | | | 10 | | | | | 15 | | |
| gag | agg | cta | ttt | ggg | tat | gat | tgg | gcg | caa | caa | acg | ata | ggg | tgt | tcg | 96 |
| Glu | Arg | Leu | Phe | Gly | Tyr | Asp | Trp | Ala | Gln | Gln | Thr | Ile | Gly | Cys | Ser | |
| | | | | 20 | | | | | 25 | | | | | 30 | | |
| gat | gcg | gcg | gta | ttt | cga | tta | tcg | gcg | caa | ggg | cga | ccg | gta | tta | ttt | 144 |
| Asp | Ala | Ala | Val | Phe | Arg | Leu | Ser | Ala | Gln | Gly | Arg | Pro | Val | Leu | Phe | |
| | | | 35 | | | | | 40 | | | | | 45 | | | |
| gta | aaa | acg | gat | tta | tcg | ggg | gcg | tta | aat | gaa | tta | caa | gat | gaa | gcg | 192 |
| Val | Lys | Thr | Asp | Leu | Ser | Gly | Ala | Leu | Asn | Glu | Leu | Gln | Asp | Glu | Ala | |
| | 50 | | | | | 55 | | | | | 60 | | | | | |
| gcg | cga | tta | tcg | tgg | tta | gcg | acg | acg | ggg | gta | ccg | tgt | gcg | gcg | gta | 240 |
| Ala | Arg | Leu | Ser | Trp | Leu | Ala | Thr | Thr | Gly | Val | Pro | Cys | Ala | Ala | Val | |
| 65 | | | | | 70 | | | | | 75 | | | | | 80 | |
| tta | gat | gta | gta | acg | gaa | gcg | ggg | cga | gat | tgg | tta | tta | tta | ggg | gaa | 288 |
| Leu | Asp | Val | Val | Thr | Glu | Ala | Gly | Arg | Asp | Trp | Leu | Leu | Leu | Gly | Glu | |
| | | | | 85 | | | | | 90 | | | | | 95 | | |
| gta | ccg | ggg | caa | gat | tta | tta | tcg | tcg | cat | tta | gcg | ccg | gcg | gaa | aaa | 336 |
| Val | Pro | Gly | Gln | Asp | Leu | Leu | Ser | Ser | His | Leu | Ala | Pro | Ala | Glu | Lys | |
| | | | | 100 | | | | | 105 | | | | | 110 | | |
| gta | tcg | ata | atg | gcg | gat | gcg | atg | cga | cga | tta | cat | acg | tta | gat | ccg | 384 |
| Val | Ser | Ile | Met | Ala | Asp | Ala | Met | Arg | Arg | Leu | His | Thr | Leu | Asp | Pro | |
| | | | 115 | | | | | 120 | | | | | 125 | | | |
| gcg | acg | tgt | ccg | ttt | gat | cat | caa | gcg | aaa | cat | cga | ata | gaa | cga | gcg | 432 |
| Ala | Thr | Cys | Pro | Phe | Asp | His | Gln | Ala | Lys | His | Arg | Ile | Glu | Arg | Ala | |
| | 130 | | | | | 135 | | | | | 140 | | | | | |
| cga | acg | cga | atg | gaa | gcg | ggg | tta | gta | gat | caa | gat | gat | tta | gat | gaa | 480 |
| Arg | Thr | Arg | Met | Glu | Ala | Gly | Leu | Val | Asp | Gln | Asp | Asp | Leu | Asp | Glu | |
| 145 | | | | | 150 | | | | | 155 | | | | | 160 | |
| gaa | cat | caa | ggg | tta | gcg | ccg | gcg | gaa | tta | ttt | gcg | cga | tta | aaa | gcg | 528 |
| Glu | His | Gln | Gly | Leu | Ala | Pro | Ala | Glu | Leu | Phe | Ala | Arg | Leu | Lys | Ala | |
| | | | | 165 | | | | | 170 | | | | | 175 | | |

```
cga atg ccg gat ggg gaa gat tta gta gta acg cat ggg gat gcg tgt        576
Arg Met Pro Asp Gly Glu Asp Leu Val Val Thr His Gly Asp Ala Cys
        180                 185                 190 tta ccg aat ata atg gta gaa aat ggg cga ttt tcg ggg ttt ata gat        624
Leu Pro Asn Ile Met Val Glu Asn Gly Arg Phe Ser Gly Phe Ile Asp
        195                 200                 205 tgt ggg cga tta ggg gta gcg gat cgt tat caa gat ata gcg tta gcg        672
Cys Gly Arg Leu Gly Val Ala Asp Arg Tyr Gln Asp Ile Ala Leu Ala
    210                 215                 220 acg cga gat ata gcg gaa gaa tta ggg ggg gaa tgg gcg gat cga ttt        720
Thr Arg Asp Ile Ala Glu Glu Leu Gly Gly Glu Trp Ala Asp Arg Phe
225                 230                 235                 240 tta gta tta tat ggg ata gcg gcg ccg gat tcg caa cga ata gcg ttt        768
Leu Val Leu Tyr Gly Ile Ala Ala Pro Asp Ser Gln Arg Ile Ala Phe
                245                 250                 255 tat cga tta tta gat gaa ttt ttt tga                                    795
Tyr Arg Leu Leu Asp Glu Phe Phe
            260

<210> SEQ ID NO 14
<211> LENGTH: 264
<212> TYPE: PRT
<213> ORGANISM: artificial
<220> FEATURE:
<223> OTHER INFORMATION: Synthetic Construct

<400> SEQUENCE: 14

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240
```

```
Leu Val Leu Tyr Gly Ile Ala Ala Pro Asp Ser Gln Arg Ile Ala Phe
            245                 250                 255

Tyr Arg Leu Leu Asp Glu Phe Phe
            260
```

<210> SEQ ID NO 15
<211> LENGTH: 417
<212> TYPE: DNA
<213> ORGANISM: artificial
<220> FEATURE:
<223> OTHER INFORMATION: anti human CD98 antibody heavy chain
<220> FEATURE:
<221> NAME/KEY: CDS
<222> LOCATION: (1)..(417)

<400> SEQUENCE: 15

```
atg aag cac ctg tgg ttc ttc ctc ctg ctg gtg gcg gct ccc aga tgg       48
Met Lys His Leu Trp Phe Phe Leu Leu Leu Val Ala Ala Pro Arg Trp
1               5                   10                  15 gtc ctg tcc cag ctg cag ctg cag gag tcg ggc cca gga ctg gtg aag       96
Val Leu Ser Gln Leu Gln Leu Gln Glu Ser Gly Pro Gly Leu Val Lys
            20                  25                  30 cct tcg gag acc ctg tcc ctc acc tgc act gtc tct ggt ggc tcc atc      144
Pro Ser Glu Thr Leu Ser Leu Thr Cys Thr Val Ser Gly Gly Ser Ile
        35                  40                  45 agc agt agt agt tac tac tgg ggc tgg atc cgc cag ccc cca ggg aag      192
Ser Ser Ser Ser Tyr Tyr Trp Gly Trp Ile Arg Gln Pro Pro Gly Lys
    50                  55                  60 ggg ctg gag tgg att ggg agt atc tat tat agt ggg agt acc tac tac      240
Gly Leu Glu Trp Ile Gly Ser Ile Tyr Tyr Ser Gly Ser Thr Tyr Tyr
65                  70                  75                  80 aac ccg tcc ctc aag agt cga gtc acc ata tcc gta gac acg tcc aag      288
Asn Pro Ser Leu Lys Ser Arg Val Thr Ile Ser Val Asp Thr Ser Lys
                85                  90                  95 aac cag ttc tcc ctg aag ctg agc tct gtg acc gcc gca gac acg gct      336
Asn Gln Phe Ser Leu Lys Leu Ser Ser Val Thr Ala Ala Asp Thr Ala
            100                 105                 110 gtg tat tac tgt gcg aga caa ggg acg ggg ctc gcc cta ttt gac tac      384
Val Tyr Tyr Cys Ala Arg Gln Gly Thr Gly Leu Ala Leu Phe Asp Tyr
        115                 120                 125 tgg ggc cag gga acc ctg gtc acc gtc tcc tca                          417
Trp Gly Gln Gly Thr Leu Val Thr Val Ser Ser
    130                 135
```

<210> SEQ ID NO 16
<211> LENGTH: 139
<212> TYPE: PRT
<213> ORGANISM: artificial
<220> FEATURE:
<223> OTHER INFORMATION: Synthetic Construct

<400> SEQUENCE: 16

```
Met Lys His Leu Trp Phe Phe Leu Leu Leu Val Ala Ala Pro Arg Trp
1               5                   10                  15

Val Leu Ser Gln Leu Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Ser Ser Tyr Tyr Trp Gly Trp Ile Arg Gln Pro Pro Gly Lys
    50                  55                  60

Gly Leu Glu Trp Ile Gly Ser Ile Tyr Tyr Ser Gly Ser Thr Tyr Tyr
```

```
                65                  70                  75                  80
Asn Pro Ser Leu Lys Ser Arg Val Thr Ile Ser Val Asp Thr Ser Lys
                    85                  90                  95

Asn Gln Phe Ser Leu Lys Leu Ser Ser Val Thr Ala Ala Asp Thr Ala
                    100                 105                 110

Val Tyr Tyr Cys Ala Arg Gln Gly Thr Gly Leu Ala Leu Phe Asp Tyr
                    115                 120                 125

Trp Gly Gln Gly Thr Leu Val Thr Val Ser Ser
            130                 135

<210> SEQ ID NO 17
<211> LENGTH: 387
<212> TYPE: DNA
<213> ORGANISM: artificial
<220> FEATURE:
<223> OTHER INFORMATION: anti human CD98 antibody light chain
<220> FEATURE:
<221> NAME/KEY: CDS
<222> LOCATION: (1)..(387)

<400> SEQUENCE: 17 atg gaa acc cca gcg cag ctt ctc ttc ctc ctg cta ctc tgg ctc cca       48
Met Glu Thr Pro Ala Gln Leu Leu Phe Leu Leu Leu Leu Trp Leu Pro
1               5                   10                  15 gat acc acc gga gaa att gtg ttg acg cag tct cca ggc acc ctg tct       96
Asp Thr Thr Gly Glu Ile Val Leu Thr Gln Ser Pro Gly Thr Leu Ser
            20                  25                  30 ttg tct cca ggg gaa aga gcc acc ctc tcc tgc agg gcc agt cag agt      144
Leu Ser Pro Gly Glu Arg Ala Thr Leu Ser Cys Arg Ala Ser Gln Ser
        35                  40                  45 gtt agc agc agc ttc tta gcc tgg tac cag cag aaa cct ggc cag gct      192
Val Ser Ser Ser Phe Leu Ala Trp Tyr Gln Gln Lys Pro Gly Gln Ala
    50                  55                  60 ccc agg ctc ctc atc tat ggt gca tcc agc agg gcc act ggc atc cca      240
Pro Arg Leu Leu Ile Tyr Gly Ala Ser Ser Arg Ala Thr Gly Ile Pro
65                  70                  75                  80 gac agg ttc agt ggc agt ggg tct ggg aca gac ttc act ctc acc atc      288
Asp Arg Phe Ser Gly Ser Gly Ser Gly Thr Asp Phe Thr Leu Thr Ile
                85                  90                  95 agc aga ctg gag cct gaa gat ttc gca gtg tat tac tgt cag cag tat      336
Ser Arg Leu Glu Pro Glu Asp Phe Ala Val Tyr Tyr Cys Gln Gln Tyr
            100                 105                 110 ggt agc tca cct cta ttc act ttc ggc cct ggg acc aaa gtg gat atc      384
Gly Ser Ser Pro Leu Phe Thr Phe Gly Pro Gly Thr Lys Val Asp Ile
        115                 120                 125 aaa                                                                  387
Lys

<210> SEQ ID NO 18
<211> LENGTH: 129
<212> TYPE: PRT
<213> ORGANISM: artificial
<220> FEATURE:
<223> OTHER INFORMATION: Synthetic Construct

<400> SEQUENCE: 18

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
```

```
                35                  40                  45
Val Ser Ser Ser Phe Leu Ala Trp Tyr Gln Gln Lys Pro Gly Gln Ala
 50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
            100                 105                 110

Gly Ser Ser Pro Leu Phe Thr Phe Gly Pro Gly Thr Lys Val Asp Ile
        115                 120                 125

Lys

<210> SEQ ID NO 19
<211> LENGTH: 600
<212> TYPE: DNA
<213> ORGANISM: unknown
<220> FEATURE:
<223> OTHER INFORMATION: wild type puromycin resistant gene
<220> FEATURE:
<221> NAME/KEY: CDS
<222> LOCATION: (1)..(600)

<400> SEQUENCE: 19 atg acc gag tac aag ccc acg gtg cgc ctc gcc acc cgc gac gac gtc     48
Met Thr Glu Tyr Lys Pro Thr Val Arg Leu Ala Thr Arg Asp Asp Val
 1               5                  10                  15 ccc cgg gcc gta cgc acc ctc gcc gcc gcg ttc gcc gac tac ccc gcc     96
Pro Arg Ala Val Arg Thr Leu Ala Ala Ala Phe Ala Asp Tyr Pro Ala
                 20                  25                  30 acg cgc cac acc gtc gac ccg gac cgc cac atc gag cgg gtc acc gag    144
Thr Arg His Thr Val Asp Pro Asp Arg His Ile Glu Arg Val Thr Glu
         35                  40                  45 ctg caa gaa ctc ttc ctc acg cgc gtc ggg ctc gac atc ggc aag gtg    192
Leu Gln Glu Leu Phe Leu Thr Arg Val Gly Leu Asp Ile Gly Lys Val
     50                  55                  60 tgg gtc gcg gac gac ggc gcc gcg gtg gcg gtc tgg acc acg ccg gag    240
Trp Val Ala Asp Asp Gly Ala Ala Val Ala Val Trp Thr Thr Pro Glu
 65                  70                  75                  80 agc gtc gaa gcg ggg gcg gtg ttc gcc gag atc ggc ccg cgc atg gcc    288
Ser Val Glu Ala Gly Ala Val Phe Ala Glu Ile Gly Pro Arg Met Ala
                 85                  90                  95 gag ttg agc ggt tcc cgg ctg gcc gcg cag caa cag atg gaa ggc ctc    336
Glu Leu Ser Gly Ser Arg Leu Ala Ala Gln Gln Gln Met Glu Gly Leu
            100                 105                 110 ctg gcg ccg cac cgg ccc aag gag ccc gcg tgg ttc ctg gcc acc gtc    384
Leu Ala Pro His Arg Pro Lys Glu Pro Ala Trp Phe Leu Ala Thr Val
        115                 120                 125 ggc gtc tcg ccc gac cac cag ggc aag ggt ctg ggc agc gcc gtc gtg    432
Gly Val Ser Pro Asp His Gln Gly Lys Gly Leu Gly Ser Ala Val Val
    130                 135                 140 ctc ccc gga gtg gag gcg gcc gag cgc gcc ggg gtg ccc gcc ttc ctg    480
Leu Pro Gly Val Glu Ala Ala Glu Arg Ala Gly Val Pro Ala Phe Leu
145                 150                 155                 160 gag acc tcc gcg ccc cgc aac ctc ccc ttc tac gag cgg ctc ggc ttc    528
Glu Thr Ser Ala Pro Arg Asn Leu Pro Phe Tyr Glu Arg Leu Gly Phe
                165                 170                 175 acc gtc acc gcc gac gtc gag gtg ccc gaa gga ccg cgc acc tgg tgc    576
Thr Val Thr Ala Asp Val Glu Val Pro Glu Gly Pro Arg Thr Trp Cys
            180                 185                 190
```

```
atg acc cgc aag ccc ggt gcc tga                                    600
Met Thr Arg Lys Pro Gly Ala
        195

<210> SEQ ID NO 20
<211> LENGTH: 199
<212> TYPE: PRT
<213> ORGANISM: unknown
<220> FEATURE:
<223> OTHER INFORMATION: Synthetic Construct

<400> SEQUENCE: 20

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195

<210> SEQ ID NO 21
<211> LENGTH: 600
<212> TYPE: DNA
<213> ORGANISM: artificial
<220> FEATURE:
<223> OTHER INFORMATION: modified puromycin resistant gene
<220> FEATURE:
<221> NAME/KEY: CDS
<222> LOCATION: (1)..(600)

<400> SEQUENCE: 21 atg acc gag tac aag ccc acg gtg cgc ctc gcg acc cgc gac gac gtc    48
Met Thr Glu Tyr Lys Pro Thr Val Arg Leu Ala Thr Arg Asp Asp Val
1               5                   10                  15 ccc cgg gcg gta cgc acc ctc gcg gcg gcg ttc gcg gac tac ccc gcg    96
Pro Arg Ala Val Arg Thr Leu Ala Ala Ala Phe Ala Asp Tyr Pro Ala
            20                  25                  30 acg cgc cac acc gtc gac ccg gac cgc cac atc gag cgg gtc acc gag   144
Thr Arg His Thr Val Asp Pro Asp Arg His Ile Glu Arg Val Thr Glu
        35                  40                  45
```

```
ctg caa gaa ctc ttc ctc acg cgc gtc ggg ctc gac atc ggc aag gtg        192
Leu Gln Glu Leu Phe Leu Thr Arg Val Gly Leu Asp Ile Gly Lys Val
     50                  55                  60 tgg gtc gcg gac gac ggc gcg gtg gcg gtc tgg acc acg ccg gag            240
Trp Val Ala Asp Asp Gly Ala Ala Val Ala Val Trp Thr Thr Pro Glu
 65                  70                  75                  80 agc gtc gaa gcg ggg gcg gtg ttc gcg gag atc ggc ccg cgc atg gcg        288
Ser Val Glu Ala Gly Ala Val Phe Ala Glu Ile Gly Pro Arg Met Ala
                 85                  90                  95 gag ttg agc ggt tcc cgg ctg gcg gcg cag caa cag atg gaa ggc ctc        336
Glu Leu Ser Gly Ser Arg Leu Ala Ala Gln Gln Gln Met Glu Gly Leu
            100                 105                 110 ctg gcg ccg cac cgg ccc aag gag ccc gcg tgg ttc ctg gcg acc gtc        384
Leu Ala Pro His Arg Pro Lys Glu Pro Ala Trp Phe Leu Ala Thr Val
        115                 120                 125 ggc gtc tcg ccc gac cac cag ggc aag ggt ctg ggc agc gcg gtc gtg        432
Gly Val Ser Pro Asp His Gln Gly Lys Gly Leu Gly Ser Ala Val Val
    130                 135                 140 ctc ccc gga gtg gag gcg gcg gag cgc gcg ggg gtg ccc gcg ttc ctg        480
Leu Pro Gly Val Glu Ala Ala Glu Arg Ala Gly Val Pro Ala Phe Leu
145                 150                 155                 160 gag acc tcc gcg ccc cgc aac ctc ccc ttc tac gag cgg ctc ggc ttc        528
Glu Thr Ser Ala Pro Arg Asn Leu Pro Phe Tyr Glu Arg Leu Gly Phe
                165                 170                 175 acc gtc acc gcg gac gtc gag gtg ccc gaa gga ccg cgc acc tgg tgc        576
Thr Val Thr Ala Asp Val Glu Val Pro Glu Gly Pro Arg Thr Trp Cys
            180                 185                 190 atg acc cgc aag ccc ggt gcg tga                                        600
Met Thr Arg Lys Pro Gly Ala
        195

<210> SEQ ID NO 22
<211> LENGTH: 199
<212> TYPE: PRT
<213> ORGANISM: artificial
<220> FEATURE:
<223> OTHER INFORMATION: Synthetic Construct

<400> SEQUENCE: 22

Met Thr Glu Tyr Lys Pro Thr Val Arg Leu Ala Thr Arg Asp Asp Val
 1               5                  10                  15

Pro Arg Ala Val Arg Thr Leu Ala Ala Ala Phe Ala Asp Tyr Pro Ala
             20                  25                  30

Thr Arg His Thr Val Asp Pro Asp Arg His Ile Glu Arg Val Thr Glu
         35                  40                  45

Leu Gln Glu Leu Phe Leu Thr Arg Val Gly Leu Asp Ile Gly Lys Val
     50                  55                  60

Trp Val Ala Asp Asp Gly Ala Ala Val Ala Val Trp Thr Thr Pro Glu
 65                  70                  75                  80

Ser Val Glu Ala Gly Ala Val Phe Ala Glu Ile Gly Pro Arg Met Ala
                 85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160
```

```
Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195

<210> SEQ ID NO 23
<211> LENGTH: 600
<212> TYPE: DNA
<213> ORGANISM: artificial
<220> FEATURE:
<223> OTHER INFORMATION: modified puromycin resistant gene
<220> FEATURE:
<221> NAME/KEY: CDS
<222> LOCATION: (1)..(600)

<400> SEQUENCE: 23 atg acc gag tac aag ccc acg gta cgc tta gcg acc cgc gac gac gta         48
Met Thr Glu Tyr Lys Pro Thr Val Arg Leu Ala Thr Arg Asp Asp Val
1               5                   10                  15 ccc cgg gcg gta cgc acc tta gcg gcg gcg ttc gcg gac tac ccc gcg         96
Pro Arg Ala Val Arg Thr Leu Ala Ala Ala Phe Ala Asp Tyr Pro Ala
            20                  25                  30 acg cgc cac acc gta gac ccg gac cgc cac atc gag cgg gta acc gag        144
Thr Arg His Thr Val Asp Pro Asp Arg His Ile Glu Arg Val Thr Glu
        35                  40                  45 tta caa gaa tta ttc tta acg cgc gta ggg tta gac atc ggc aag gta        192
Leu Gln Glu Leu Phe Leu Thr Arg Val Gly Leu Asp Ile Gly Lys Val
    50                  55                  60 tgg gta gcg gac gac ggc gcg gcg gta gcg gta tgg acc acg ccg gag        240
Trp Val Ala Asp Asp Gly Ala Ala Val Ala Val Trp Thr Thr Pro Glu
65                  70                  75                  80 tcg gta gaa gcg ggg gcg gta ttc gcg gag atc ggc ccg cgc atg gcg        288
Ser Val Glu Ala Gly Ala Val Phe Ala Glu Ile Gly Pro Arg Met Ala
                85                  90                  95 gag tta tcg ggt tcg cgg tta gcg gcg cag caa cag atg gaa ggc tta        336
Glu Leu Ser Gly Ser Arg Leu Ala Ala Gln Gln Gln Met Glu Gly Leu
            100                 105                 110 tta gcg ccg cac cgg ccc aag gag ccc gcg tgg ttc tta gcg acc gta        384
Leu Ala Pro His Arg Pro Lys Glu Pro Ala Trp Phe Leu Ala Thr Val
        115                 120                 125 ggc gta tcg ccc gac cac cag ggc aag ggt tta ggc tcg gcg gta gta        432
Gly Val Ser Pro Asp His Gln Gly Lys Gly Leu Gly Ser Ala Val Val
    130                 135                 140 tta ccc gga gta gag gcg gcg gag cgc gcg ggg gta ccc gcg ttc tta        480
Leu Pro Gly Val Glu Ala Ala Glu Arg Ala Gly Val Pro Ala Phe Leu
145                 150                 155                 160 gag acc tcg gcg ccc cgc aac tta ccc ttc tac gag cgg tta ggc ttc        528
Glu Thr Ser Ala Pro Arg Asn Leu Pro Phe Tyr Glu Arg Leu Gly Phe
                165                 170                 175 acc gta acc gcg gac gta gag gta ccc gaa gga ccg cgc acc tgg tgc        576
Thr Val Thr Ala Asp Val Glu Val Pro Glu Gly Pro Arg Thr Trp Cys
            180                 185                 190 atg acc cgc aag ccc ggt gcg tga                                        600
Met Thr Arg Lys Pro Gly Ala
        195

<210> SEQ ID NO 24
<211> LENGTH: 199
<212> TYPE: PRT
```

<213> ORGANISM: artificial
<220> FEATURE:
<223> OTHER INFORMATION: Synthetic Construct

<400> SEQUENCE: 24

```
Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195
```

<210> SEQ ID NO 25
<211> LENGTH: 600
<212> TYPE: DNA
<213> ORGANISM: artificial
<220> FEATURE:
<223> OTHER INFORMATION: modified puromycin resistant gene
<220> FEATURE:
<221> NAME/KEY: CDS
<222> LOCATION: (1)..(600)

<400> SEQUENCE: 25

```
atg acg gaa tat aaa ccg acg gta cgt tta gcg acg cgt gat gat gta      48
Met Thr Glu Tyr Lys Pro Thr Val Arg Leu Ala Thr Arg Asp Asp Val
1               5                   10                  15 ccg cgt gcg gta cgt acg tta gcg gcg gcg ttt gcg gat tat ccg gcg      96
Pro Arg Ala Val Arg Thr Leu Ala Ala Ala Phe Ala Asp Tyr Pro Ala
            20                  25                  30 acg cgt cat acg gta gat ccg gat cgt cat ata gaa cgt gta acg gaa     144
Thr Arg His Thr Val Asp Pro Asp Arg His Ile Glu Arg Val Thr Glu
        35                  40                  45 tta caa gaa tta ttt tta acg cgt gta ggt tta gat ata ggt aaa gta     192
Leu Gln Glu Leu Phe Leu Thr Arg Val Gly Leu Asp Ile Gly Lys Val
50                  55                  60 tgg gta gcg gat gat ggt gcg gcg gta gcg gta tgg acg acg ccg gaa     240
Trp Val Ala Asp Asp Gly Ala Ala Val Ala Val Trp Thr Thr Pro Glu
65                  70                  75                  80 tcg gta gaa gcg ggt gcg gta ttt gcg gaa ata ggt ccg cgt atg gcg     288
```

```
Ser Val Glu Ala Gly Ala Val Phe Ala Glu Ile Gly Pro Arg Met Ala
             85                  90                  95 gaa tta tcg ggt tcg cgt tta gcg gcg caa caa caa atg gaa ggt tta       336
Glu Leu Ser Gly Ser Arg Leu Ala Ala Gln Gln Gln Met Glu Gly Leu
            100                 105                 110 tta gcg ccg cat cgt ccg aaa gaa ccg gcg tgg ttt tta gcg acg gta       384
Leu Ala Pro His Arg Pro Lys Glu Pro Ala Trp Phe Leu Ala Thr Val
            115                 120                 125 ggt gta tcg ccg gat cat caa ggt aaa ggt tta ggt tcg gcg gta gta       432
Gly Val Ser Pro Asp His Gln Gly Lys Gly Leu Gly Ser Ala Val Val
        130                 135                 140 tta ccg ggt gta gaa gcg gcg gaa cgt gcg ggt gta ccg gcg ttt tta       480
Leu Pro Gly Val Glu Ala Ala Glu Arg Ala Gly Val Pro Ala Phe Leu
145                 150                 155                 160 gaa acg tcg gcg ccg cgt aat tta ccg ttt tat gaa cgt tta ggt ttt       528
Glu Thr Ser Ala Pro Arg Asn Leu Pro Phe Tyr Glu Arg Leu Gly Phe
                165                 170                 175 acg gta acg gcg gat gta gaa gta ccg gaa ggt ccg cgt acg tgg tgt       576
Thr Val Thr Ala Asp Val Glu Val Pro Glu Gly Pro Arg Thr Trp Cys
                180                 185                 190 atg acg cgt aaa ccg ggt gcg tga                                       600
Met Thr Arg Lys Pro Gly Ala
            195

<210> SEQ ID NO 26
<211> LENGTH: 199
<212> TYPE: PRT
<213> ORGANISM: artificial
<220> FEATURE:
<223> OTHER INFORMATION: Synthetic Construct

<400> SEQUENCE: 26

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195
```

<210> SEQ ID NO 27
<211> LENGTH: 375
<212> TYPE: DNA
<213> ORGANISM: artificial
<220> FEATURE:
<223> OTHER INFORMATION: modified zeocin resistant gene
<220> FEATURE:
<221> NAME/KEY: CDS
<222> LOCATION: (1)..(375)

<400> SEQUENCE: 27

```
atg gcg aag tta acc tcg gcg gtt ccg gta tta acc gcg cgc gac gtc      48
Met Ala Lys Leu Thr Ser Ala Val Pro Val Leu Thr Ala Arg Asp Val
1               5                   10                  15 gcg gga gcg gtc gag ttc tgg acc gac cgg tta ggg ttc tcg cgg gac      96
Ala Gly Ala Val Glu Phe Trp Thr Asp Arg Leu Gly Phe Ser Arg Asp
            20                  25                  30 ttc gta gag gac gac ttc gcg ggt gta gtc cgg gac gac gta acc tta     144
Phe Val Glu Asp Asp Phe Ala Gly Val Val Arg Asp Asp Val Thr Leu
        35                  40                  45 ttc atc tcg gcg gtc cag gac cag gta gta ccg gac aac acc tta gcg     192
Phe Ile Ser Ala Val Gln Asp Gln Val Val Pro Asp Asn Thr Leu Ala
    50                  55                  60 tgg gta tgg gta cgc ggc tta gac gag tta tac gcg gag tgg tcg gag     240
Trp Val Trp Val Arg Gly Leu Asp Glu Leu Tyr Ala Glu Trp Ser Glu
65                  70                  75                  80 gtc gta tcg acg aac ttc cgg gac gcc tcg ggg ccg gcg atg acc gag     288
Val Val Ser Thr Asn Phe Arg Asp Ala Ser Gly Pro Ala Met Thr Glu
                85                  90                  95 atc ggc gag cag ccg tgg ggg cgg gag ttc gcg tta cgc gac ccg gcg     336
Ile Gly Glu Gln Pro Trp Gly Arg Glu Phe Ala Leu Arg Asp Pro Ala
            100                 105                 110 ggc aac tgc gta cac ttc gta gcg gag gag cag gac tga                 375
Gly Asn Cys Val His Phe Val Ala Glu Glu Gln Asp
        115                 120
```

<210> SEQ ID NO 28
<211> LENGTH: 124
<212> TYPE: PRT
<213> ORGANISM: artificial
<220> FEATURE:
<223> OTHER INFORMATION: Synthetic Construct

<400> SEQUENCE: 28

```
Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120
```

<210> SEQ ID NO 29
<211> LENGTH: 375
<212> TYPE: DNA
<213> ORGANISM: artificial
<220> FEATURE:
<223> OTHER INFORMATION: modified zeocin resistant gene
<220> FEATURE:
<221> NAME/KEY: CDS
<222> LOCATION: (1)..(375)

<400> SEQUENCE: 29

```
atg gcg aaa tta acg tcg gcg gta ccg gta tta acg gcg cgt gat gta      48
Met Ala Lys Leu Thr Ser Ala Val Pro Val Leu Thr Ala Arg Asp Val
1               5                   10                  15 gcg ggt gcg gta gaa ttt tgg acg gat cgt tta ggt ttt tcg cgt gat      96
Ala Gly Ala Val Glu Phe Trp Thr Asp Arg Leu Gly Phe Ser Arg Asp
            20                  25                  30 ttt gta gaa gat gat ttt gcg ggt gta gta cgt gat gat gta acg tta     144
Phe Val Glu Asp Asp Phe Ala Gly Val Val Arg Asp Asp Val Thr Leu
        35                  40                  45 ttt ata tcg gcg gta caa gat caa gta gta ccg gat aat acg tta gcg     192
Phe Ile Ser Ala Val Gln Asp Gln Val Val Pro Asp Asn Thr Leu Ala
    50                  55                  60 tgg gta tgg gta cgt ggt tta gat gaa tta tat gcg gaa tgg tcg gaa     240
Trp Val Trp Val Arg Gly Leu Asp Glu Leu Tyr Ala Glu Trp Ser Glu
65                  70                  75                  80 gta gta tcg acg aat ttt cgt gat gcg tcg ggt ccg gcg atg acg gaa     288
Val Val Ser Thr Asn Phe Arg Asp Ala Ser Gly Pro Ala Met Thr Glu
                85                  90                  95 ata ggt gaa caa ccg tgg ggt cgt gaa ttt gcg tta cgt gat ccg gcg     336
Ile Gly Glu Gln Pro Trp Gly Arg Glu Phe Ala Leu Arg Asp Pro Ala
            100                 105                 110 ggt aat tgt gta cat ttt gta gcg gaa gaa caa gat tga                 375
Gly Asn Cys Val His Phe Val Ala Glu Glu Gln Asp
        115                 120
```

<210> SEQ ID NO 30
<211> LENGTH: 124
<212> TYPE: PRT
<213> ORGANISM: artificial
<220> FEATURE:
<223> OTHER INFORMATION: Synthetic Construct

<400> SEQUENCE: 30

```
Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120
```

```
<210> SEQ ID NO 31
<211> LENGTH: 1026
<212> TYPE: DNA
<213> ORGANISM: artificial
<220> FEATURE:
<223> OTHER INFORMATION: modified hygromycin resistant gene
<220> FEATURE:
<221> NAME/KEY: CDS
<222> LOCATION: (1)..(1026)

<400> SEQUENCE: 31
```

| | | | | | | | | | | | | | | | | |
|---|---|---|---|---|---|---|---|---|---|---|---|---|---|---|---|---|
| atg | aaa | aag | cct | gaa | tta | acc | gcg | acg | tcg | gta | gag | aag | ttt | tta | atc | 48 |
| Met | Lys | Lys | Pro | Glu | Leu | Thr | Ala | Thr | Ser | Val | Glu | Lys | Phe | Leu | Ile | |
| 1 | | | | 5 | | | | | 10 | | | | | 15 | | |
| gaa | aag | ttc | gac | tcg | gta | tcg | gac | tta | atg | cag | tta | tcg | gag | ggc | gaa | 96 |
| Glu | Lys | Phe | Asp | Ser | Val | Ser | Asp | Leu | Met | Gln | Leu | Ser | Glu | Gly | Glu | |
| | | | 20 | | | | | 25 | | | | | 30 | | | |
| gaa | tcg | cgt | gcg | ttc | tcg | ttc | gat | gta | gga | ggg | cgt | gga | tat | gta | tta | 144 |
| Glu | Ser | Arg | Ala | Phe | Ser | Phe | Asp | Val | Gly | Gly | Arg | Gly | Tyr | Val | Leu | |
| | | 35 | | | | | 40 | | | | | 45 | | | | |
| cgt | gta | aat | tcg | tgc | gcg | gat | ggt | ttc | tac | aaa | gat | cgt | tat | gta | tat | 192 |
| Arg | Val | Asn | Ser | Cys | Ala | Asp | Gly | Phe | Tyr | Lys | Asp | Arg | Tyr | Val | Tyr | |
| 50 | | | | 55 | | | | | 60 | | | | | | | |
| cgt | cac | ttt | gcg | tcg | gcg | gcg | tta | ccg | att | ccg | gaa | gta | tta | gac | att | 240 |
| Arg | His | Phe | Ala | Ser | Ala | Ala | Leu | Pro | Ile | Pro | Glu | Val | Leu | Asp | Ile | |
| 65 | | | | | 70 | | | | | 75 | | | | | 80 | |
| ggg | gaa | ttc | tcg | gag | tcg | tta | acc | tat | tgc | atc | tcg | cgc | cgt | gcg | cag | 288 |
| Gly | Glu | Phe | Ser | Glu | Ser | Leu | Thr | Tyr | Cys | Ile | Ser | Arg | Arg | Ala | Gln | |
| | | | | 85 | | | | | 90 | | | | | 95 | | |
| ggt | gta | acg | ttg | caa | gac | tta | cct | gaa | acc | gaa | tta | ccc | gcg | gta | tta | 336 |
| Gly | Val | Thr | Leu | Gln | Asp | Leu | Pro | Glu | Thr | Glu | Leu | Pro | Ala | Val | Leu | |
| | | | | 100 | | | | | 105 | | | | | 110 | | |
| cag | ccg | gta | gcg | gag | gcg | atg | gat | gcg | atc | gcg | gcg | gcg | gat | tta | tcg | 384 |
| Gln | Pro | Val | Ala | Glu | Ala | Met | Asp | Ala | Ile | Ala | Ala | Ala | Asp | Leu | Ser | |
| | | | 115 | | | | | 120 | | | | | 125 | | | |
| cag | acg | tcg | ggg | ttc | ggc | cca | ttc | gga | ccg | caa | gga | atc | ggt | caa | tac | 432 |
| Gln | Thr | Ser | Gly | Phe | Gly | Pro | Phe | Gly | Pro | Gln | Gly | Ile | Gly | Gln | Tyr | |
| | | 130 | | | | | 135 | | | | | 140 | | | | |
| act | aca | tgg | cgt | gat | ttc | ata | tgc | gcg | att | gcg | gat | ccc | cat | gta | tat | 480 |
| Thr | Thr | Trp | Arg | Asp | Phe | Ile | Cys | Ala | Ile | Ala | Asp | Pro | His | Val | Tyr | |
| 145 | | | | | 150 | | | | | 155 | | | | | 160 | |
| cac | tgg | caa | act | gta | atg | gac | gac | acc | gta | tcg | gcg | tcg | gta | gcg | cag | 528 |
| His | Trp | Gln | Thr | Val | Met | Asp | Asp | Thr | Val | Ser | Ala | Ser | Val | Ala | Gln | |
| | | | | 165 | | | | | 170 | | | | | 175 | | |
| gcg | tta | gat | gag | tta | atg | tta | tgg | gcg | gag | gac | tgc | ccc | gaa | gta | cgt | 576 |
| Ala | Leu | Asp | Glu | Leu | Met | Leu | Trp | Ala | Glu | Asp | Cys | Pro | Glu | Val | Arg | |
| | | | 180 | | | | | 185 | | | | | 190 | | | |
| cac | tta | gta | cac | gcg | gat | ttc | ggc | tcg | aac | aat | gta | tta | acg | gac | aat | 624 |
| His | Leu | Val | His | Ala | Asp | Phe | Gly | Ser | Asn | Asn | Val | Leu | Thr | Asp | Asn | |
| | | 195 | | | | | 200 | | | | | 205 | | | | |
| ggc | cgc | ata | aca | gcg | gta | att | gac | tgg | tcg | gag | gcg | atg | ttc | ggg | gat | 672 |
| Gly | Arg | Ile | Thr | Ala | Val | Ile | Asp | Trp | Ser | Glu | Ala | Met | Phe | Gly | Asp | |
| | | 210 | | | | | 215 | | | | | 220 | | | | |
| tcg | caa | tac | gag | gta | gcg | aac | atc | ttc | ttc | tgg | cgt | ccg | tgg | ttg | gcg | 720 |
| Ser | Gln | Tyr | Glu | Val | Ala | Asn | Ile | Phe | Phe | Trp | Arg | Pro | Trp | Leu | Ala | |
| 225 | | | | | 230 | | | | | 235 | | | | | 240 | |
| tgt | atg | gag | cag | cag | acg | cgc | tac | ttc | gag | cgt | cgt | cat | ccg | gag | tta | 768 |
| Cys | Met | Glu | Gln | Gln | Thr | Arg | Tyr | Phe | Glu | Arg | Arg | His | Pro | Glu | Leu | |
| | | | | 245 | | | | | 250 | | | | | 255 | | |
| gcg | gga | tcg | ccg | cgt | tta | cgt | gcg | tat | atg | tta | cgc | att | ggt | ctt | gac | 816 |

```
                    Ala Gly Ser Pro Arg Leu Arg Ala Tyr Met Leu Arg Ile Gly Leu Asp
                                    260                 265                 270 caa tta tat cag tcg ttg gta gac ggc aat ttc gat gat gcg gcg tgg            864
Gln Leu Tyr Gln Ser Leu Val Asp Gly Asn Phe Asp Asp Ala Ala Trp
                275                 280                 285 gcg cag ggt cga tgc gac gcg atc gta cga tcg gga gcg ggg act gta            912
Ala Gln Gly Arg Cys Asp Ala Ile Val Arg Ser Gly Ala Gly Thr Val
        290                 295                 300 ggg cgt aca caa atc gcg cgc cgt tcg gcg gcg gta tgg acc gat ggc            960
Gly Arg Thr Gln Ile Ala Arg Arg Ser Ala Ala Val Trp Thr Asp Gly
305                 310                 315                 320 tgt gta gaa gta tta gcg gat tcg gga aac cga cgc ccc tcg act cgt           1008
Cys Val Glu Val Leu Ala Asp Ser Gly Asn Arg Arg Pro Ser Thr Arg
                325                 330                 335 ccg cgt gcg aag gaa tag                                                   1026
Pro Arg Ala Lys Glu
                340

<210> SEQ ID NO 32
<211> LENGTH: 341
<212> TYPE: PRT
<213> ORGANISM: artificial
<220> FEATURE:
<223> OTHER INFORMATION: Synthetic Construct

<400> SEQUENCE: 32

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
                20                  25                  30

Glu Ser Arg Ala Phe Ser Phe Asp Val Gly Gly Arg Gly Tyr Val Leu
            35                  40                  45

Arg Val Asn Ser Cys Ala Asp Gly Phe Tyr Lys Asp Arg Tyr Val Tyr
        50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
```

```
                        245                 250                 255
Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340

<210> SEQ ID NO 33
<211> LENGTH: 1026
<212> TYPE: DNA
<213> ORGANISM: artificial
<220> FEATURE:
<223> OTHER INFORMATION: modified hygromycin resistant gene
<220> FEATURE:
<221> NAME/KEY: CDS
<222> LOCATION: (1)..(1026)

<400> SEQUENCE: 33 atg aaa aaa ccg gaa tta acg gcg acg tcg gta gaa aaa ttt tta ata       48
Met Lys Lys Pro Glu Leu Thr Ala Thr Ser Val Glu Lys Phe Leu Ile
1               5                   10                  15 gaa aaa ttt gat tcg gta tcg gat tta atg caa tta tcg gaa ggt gaa       96
Glu Lys Phe Asp Ser Val Ser Asp Leu Met Gln Leu Ser Glu Gly Glu
            20                  25                  30 gaa tcg cgt gcg ttt tcg ttt gat gta ggt ggt cgt ggt tat gta tta      144
Glu Ser Arg Ala Phe Ser Phe Asp Val Gly Gly Arg Gly Tyr Val Leu
        35                  40                  45 cgt gta aat tcg tgt gcg gat ggt ttt tat aaa gat cgt tat gta tat      192
Arg Val Asn Ser Cys Ala Asp Gly Phe Tyr Lys Asp Arg Tyr Val Tyr
    50                  55                  60 cgt cat ttt gcg tcg gcg gcg tta ccg ata ccg gaa gta tta gat ata      240
Arg His Phe Ala Ser Ala Ala Leu Pro Ile Pro Glu Val Leu Asp Ile
65                  70                  75                  80 ggt gaa ttt tcg gaa tcg tta acg tat tgt ata tcg cgt cgt gcg caa      288
Gly Glu Phe Ser Glu Ser Leu Thr Tyr Cys Ile Ser Arg Arg Ala Gln
                85                  90                  95 ggt gta acg tta caa gat tta ccg gaa acg gaa tta ccg gcg gta tta      336
Gly Val Thr Leu Gln Asp Leu Pro Glu Thr Glu Leu Pro Ala Val Leu
            100                 105                 110 caa ccg gta gcg gaa gcg atg gat gcg ata gcg gcg gat tta tcg          384
Gln Pro Val Ala Glu Ala Met Asp Ala Ile Ala Ala Asp Leu Ser
        115                 120                 125 caa acg tcg ggt ttt ggt ccg ttt ggt ccg caa ggt ata ggt caa tat      432
Gln Thr Ser Gly Phe Gly Pro Phe Gly Pro Gln Gly Ile Gly Gln Tyr
    130                 135                 140 acg acg tgg cgt gat ttt ata tgt gcg ata gcg gat ccg cat gta tat      480
Thr Thr Trp Arg Asp Phe Ile Cys Ala Ile Ala Asp Pro His Val Tyr
145                 150                 155                 160 cat tgg caa acg gta atg gat gat acg gta tcg gcg tcg gta gcg caa      528
His Trp Gln Thr Val Met Asp Asp Thr Val Ser Ala Ser Val Ala Gln
                165                 170                 175 gcg tta gat gaa tta atg tta tgg gcg gaa gat tgt ccg gaa gta cgt      576
Ala Leu Asp Glu Leu Met Leu Trp Ala Glu Asp Cys Pro Glu Val Arg
```

```
                180                 185                 190
cat tta gta cat gcg gat ttt ggt tcg aat aat gta tta acg gat aat      624
His Leu Val His Ala Asp Phe Gly Ser Asn Asn Val Leu Thr Asp Asn
            195                 200                 205 ggt cgt ata acg gcg gta ata gat tgg tcg gaa gcg atg ttt ggt gat      672
Gly Arg Ile Thr Ala Val Ile Asp Trp Ser Glu Ala Met Phe Gly Asp
210                 215                 220 tcg caa tat gaa gta gcg aat ata ttt ttt tgg cgt ccg tgg tta gcg      720
Ser Gln Tyr Glu Val Ala Asn Ile Phe Phe Trp Arg Pro Trp Leu Ala
225                 230                 235                 240 tgt atg gaa caa caa acg cgt tat ttt gaa cgt cgt cat ccg gaa tta      768
Cys Met Glu Gln Gln Thr Arg Tyr Phe Glu Arg Arg His Pro Glu Leu
            245                 250                 255 gcg ggt tcg ccg cgt tta cgt gcg tat atg tta cgt ata ggt tta gat      816
Ala Gly Ser Pro Arg Leu Arg Ala Tyr Met Leu Arg Ile Gly Leu Asp
                260                 265                 270 caa tta tat caa tcg tta gta gat ggt aat ttt gat gat gcg gcg tgg      864
Gln Leu Tyr Gln Ser Leu Val Asp Gly Asn Phe Asp Asp Ala Ala Trp
            275                 280                 285 gcg caa ggt cgt tgt gat gcg ata gta cgt tcg ggt gcg ggt acg gta      912
Ala Gln Gly Arg Cys Asp Ala Ile Val Arg Ser Gly Ala Gly Thr Val
290                 295                 300 ggt cgt acg caa ata gcg cgt cgt tcg gcg gcg gta tgg acg gat ggt      960
Gly Arg Thr Gln Ile Ala Arg Arg Ser Ala Ala Val Trp Thr Asp Gly
305                 310                 315                 320 tgt gta gaa gta tta gcg gat tcg ggt aat cgt cgt ccg tcg acg cgt     1008
Cys Val Glu Val Leu Ala Asp Ser Gly Asn Arg Arg Pro Ser Thr Arg
                325                 330                 335 ccg cgt gcg aaa gaa tga                                             1026
Pro Arg Ala Lys Glu
            340

<210> SEQ ID NO 34
<211> LENGTH: 341
<212> TYPE: PRT
<213> ORGANISM: artificial
<220> FEATURE:
<223> OTHER INFORMATION: Synthetic Construct

<400> SEQUENCE: 34

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140
```

```
Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
            195                 200                 205

Gly Arg Ile Thr Ala Val Ile Asp Trp Ser Glu Ala Met Phe Gly Asp
210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
            275                 280                 285

Ala Gln Gly Arg Cys Asp Ala Ile Val Arg Ser Gly Ala Gly Thr Val
290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340

<210> SEQ ID NO 35
<211> LENGTH: 200
<212> TYPE: DNA
<213> ORGANISM: artificial
<220> FEATURE:
<223> OTHER INFORMATION: Tol1-L transposon sequence

<400> SEQUENCE: 35
cagtagcggt tctaggcacg ggccgtccgg gcggtggcct ggggcggaaa actgaagggg      60
ggcggcaccg gcggctcagc cctttgtaat atattaatat gcaccactat tggtttactt     120
atgtcacagt ttgtaagttt gtaacagcct gaacctggcc gcgccgccgc cctcgccccg     180
cagctgcgct ctcctgtctt                                                  200

<210> SEQ ID NO 36
<211> LENGTH: 505
<212> TYPE: DNA
<213> ORGANISM: artificial
<220> FEATURE:
<223> OTHER INFORMATION: Tol1-R transposon sequence

<400> SEQUENCE: 36 atattttag ccaatagaat ttccataaat ctgtaggtag ttttaaaaat gaatatttac       60
catttactgc aactctatgg ggacaaaaca taatgtaaca ggtcataact aaaaatgtgc    120
caatcaaagg attgaagacg gaaaacatga gttaattttt cttctctgaa gtagagatcg    180
atatagaaca tgacaattta aatttccaat tcataaatgt ttttaaaata tttattttat    240
attatttatt taacattgag tttgattcaa tattttctta gctaactgta tttttgccat    300
gcttatggtc ttttattttt tgtgttctga taacttttat aatgctttc agaattttga    360
```

```
catcttttgt atccacttct taatttcaat gacaataaaa catttcagtt gacgaagaca    420
aacaaagttc tgttgtgact atggggggggg ggggcgcctg gggatggtct cgcccgggga    480
gtaattcagg gtagaaccgc cactg                                          505
```

<210> SEQ ID NO 37
<211> LENGTH: 1855
<212> TYPE: DNA
<213> ORGANISM: artificial
<220> FEATURE:
<223> OTHER INFORMATION: nonautologus Tol1 transposon

<400> SEQUENCE: 37

```
cagtagcggt tctaggcacg ggccgtccgg gcggtggcct ggggcggaaa actgaagggg     60
ggcggcaccg gcggctcagc cctttgtaat atattaatat gcaccactat tggtttactt    120
atgtcacagt ttgtaagttt gtaacagcct gaacctggcc gcgccgccgc cctcgccccg    180
cagctgcgct ctcctgtctt tgagaagtag acacaaatgt gtgtgaagaa ggagaaggga    240
gggggcgcgg ggtgagcacg gagcgtcgcc gcgtttgcgc atgcgcaaaa cctggctggc    300 tcatcttttca ggggaggcga cggtcgcggg cttgatgaaa aaaataaaag taaaaactgc    360
gactgcgccg tcatgtagcg aatcagcgcc cctggctgta gctgcacgcg ctcctgctgg    420
aaatgtgtga agagggggg ggggggggg gctgcgggga atcagttcaa ttgtgggacg     480
cttccaaatt aagtggctag gtggggacaa gggcgggggt tgaatctac ttcataaaac    540 cttttatat tataagtcag tcataaggtg acattctata acctacatttt taataaaggt    600 ataaaaata tattctgctt ttttttgggtt aattttgtgt gaaatgtcca aataaaaaaa    660
atggcaacac aaaacaatgc tgtcactaag gtgacagttg gttcagtcga cggacttgat    720
gccttcttcg tgacgtgagg acattatgc caaacaaacg ccaataaaca tctaaaatat    780
ggaaaagaaa aggtcaaagc catctggtgc ccaatttaga agaaaagaa agaagaaga    840 ggagaaaaga gataaagaaa agggtaagtc ctcacagctt gatgcatgtt ttttctaaat    900
tctaatgcta cctgccctac aacaacgttg ccgatgaaaa ctttatttttg gtcgatgacc    960 aacactgaat taggcccaaa tgttgcaaat agcgtcattt tttttttttt ttttagattt   1020
tattcttaaa aatttgctct gccttaactt gtaacattag ttatgattca tgtgtctgtc   1080
tgctctgctg taacacaaag gttttgttgg gttttgctgt tgtatactag ctcataatgt   1140 taaaaagct gtgatggtta cacagcatgc tggtgctgcc ataagatgct aatggggcaa   1200
ataatttgag attggtcatt aatttaataa tcatttgtgg cagcctaaac gttttcacaa   1260 tgttttttttg acatttaact ggggatttag gggttaattt tgagcctgca tatgaagttt   1320 atttttttatt tgttttacaa atgtgggatt atatttttag ccaatagaat ttccataaat   1380
ctgtaggtag ttttaaaaat gaatatttac catttactgc aactctatgg ggacaaaaca   1440
taatgtaaca ggtcataact aaaaatgtgc caatcaaagg attgaagacg gaaaacatga   1500 gttaatttttt cttctctgaa gtagagatcg atatagaaca tgacaattta aatttccaat   1560
tcataaatgt ttttaaaaata tttatttttat attatttatt taacattgag tttgattcaa   1620
tattttctta gctaactgta tttttgccat gcttatggtc ttttattttt tgtgttctga   1680
taacttttat aatgcttttc agaatttga catcttttgt atccacttct taatttcaat   1740
gacaataaaa catttcagtt gacgaagaca aacaaagttc tgttgtgact atggggggg   1800 ggggcgcctg gggatggtct cgcccgggga gtaattcagg gtagaaccgc cactg        1855
```

METHOD FOR PRODUCING PROTEINS

TECHNICAL FIELD

This invention relates to a method for producing a protein of interest, comprising introducing an expression vector which comprises a gene fragment comprising a DNA encoding the protein of interest and a selectable marker gene and also comprises a pair of transposon sequences at both terminals of the gene fragment, into a suspension mammalian cell; integrating the gene fragment inserted between the pair of transposon sequences into a chromosome of the mammalian cell; obtaining a suspension mammalian cell producing the protein of interest; and suspension-culturing the mammalian cell, and a suspension mammalian cell which expresses the protein of interest by the method.

BACKGROUND ART

Production of exogenous proteins by recombinant DNA techniques is used in various industries such as pharmaceutical industry and food industry. In most cases, production of recombinant proteins is carried out by introducing an expression vector comprising a nucleotide sequence encoding a protein of interest into a host, such as *Escherichia coli*, yeast, insect cell, plant cell, and animal cell, selecting a transformant in which the expression vector is integrated into the chromosome, and further culturing the transformed cell line under appropriate culture conditions.

However, in order to develop a host which can produce an exogenous protein efficiently, it is necessary to select a host cell having good productivity for each protein of interest, so that a further technical innovation is desired on the exogenous protein production techniques for each host.

In the bacteria systems, such as *Escherichia coli*, or yeast systems, different from animal cells, post-translational modifications, such as sugar chain modification, are difficult to attain in many cases and thus cause a problem in producing a protein having its activity.

Since the produced protein is subject to a post-translational modification such as phosphorylation and addition of sugar chains in the insect system, this system has a merit that the protein having its original physiological activity can be expressed. However, since the sugar chain structure of the secreted protein is different from that of mammalians-derived cells, antigenicity and the like become a problem when the protein is applied to pharmaceutical use.

In addition, since a recombinant virus is used in the insect cell system when an exogenous gene is introduced, there is a problem that its inactivation and containment of the virus are required from the viewpoint of safety.

In the animal cell system, post-translational modifications, such as phosphorylation, sugar chain addition, and folding, can be conducted to proteins derived from higher animals including human, in more similar manner to those produced in the living body. Such accurate post-translational modifications are necessary for recreating the physiological activity originally possessed by a protein in its recombinant protein, and a protein production system in which a mammalian cell is used as a host is usually applied to pharmaceutical products and the like that requires such physiological activity.

However, a protein expression system in which a mammalian cell is used as the host is generally low in productivity, and also causes a problem of the stability of introduced genes in many cases. Improvement of productivity of a protein using a mammalian culture cell as a host is not only very important in producing medicaments for treatment, diagnostic agents and the like, but also greatly contributes to research and development of them. Thus, it is urgent to develop a gene expression system which easily makes it possible to obtain a cell line of a high productivity using a mammalian culture cell, particularly Chinese hamster ovary cell (CHO cell), as the host.

A transposon is a transposable genetic element which can move from one locus to other locus on the chromosome. A transposon is a strong tool for the study on molecular biology and genetics and used for a purpose, such as mutagenesis, gene trapping, and preparation of transgenic individuals, in insects or nematode (e.g., *Drosophila melanogaster* or *Caenorhabditis elegans*) and plants. However, development of such a technique has been delayed for vertebral animals including mammalian cells.

In recent years, however, transposons which have activities also in vertebral animals have been reported, and some of them were shown to have an activity in mammalian cells, such as cell derived from mouse and human. Typical examples include transposons Tol1 (Patent Reference 1) and Tol2 (Non-patent Reference 1) which are cloned from a medaka (killifish), Sleeping Beauty reconstructed from a non-autonomous transposon existed in *Onchorhynchus* fish genome (Non-patent Reference 2), an artificial transposon Frog prince (Non-patent Reference 3) which is derived from frog, and a transposon piggyBac (Non-patent Reference 4) which is derived from insect.

These DNA transposons have been used for mutagenesis, gene trapping, preparation of transgenic individuals, expression of drug-resistant proteins, and the like, as a gene introduction tool for bringing a new phenotype in a genome of a mammalian cell (Non-patent References 5 to 12).

In the case of insects, a method in which an exogenous gene is introduced into silkworm chromosome using the transposon piggyBac derived from a *Lepidoptera* insect to express the protein encoded by said exogenous gene has been studied, and a protein production method using the above techniques was disclosed (Patent Reference 2).

However, since protein of interest is not expressed at sufficient levels and is produced in the whole body of silkworm, it causes an economical problem due to the necessity of an advanced purification technique for recovering the expressed exogenous protein in a highly purified form from the body fluid including a large amount of contaminated proteins.

In addition, an example in which a protein relating to G418 resistance is expressed in a mammalian cell using the medaka-derived transposon Tol2 (Non-patent Reference 12) is known.

As one method for efficiently screening high expression cells, attenuation of a selectable marker gene is known. As a method for attenuation, amino acid modification in a neomycin resistance gene (Non-patent References 13 and 14) and binding of a destabilization sequence in dhfr gene (Non-patent Reference 15) are known. Alternatively, it is shown that high expression cells can be obtained by using an attenuated selectable marker gene.

On the other hand, it is also shown that the number of drug-resistant cells is drastically reduced by the attenuation and that, as a result, there is a possibility of not obtaining any drug-resistant cell. Thus, creation of a method for efficiently screening high expression cells is still desired.

It is known that in protein coding genes, there is codon usage bias depending on species and that human erythropoiethin expression in a CHO cell is improved by optimizing this codon bias (Non-patent Reference 16).

CITATION LIST

Patent Literature

[Patent Literature 1] WO 2008/072540
[Patent Literature 2] Japanese Published Unexamined Patent Application No. 2001-532188

Non Patent Literature

[Non Patent Literature 1] *Nature* 383, 30 (1996)
[Non Patent Literature 2] *Cell* 91, 501-510 (1997)
[Non Patent Literature 3] *Nucleic Acids Res,* 31, 6873-6881 (2003)
[Non Patent Literature 4] *Insect Mol. Biol.* 5, 141-151 (1996)
[Non Patent Literature 5] *Genetics.* 166, 895-899 (2004)
[Non Patent Literature 6] *PLoS Genet,* 2, e169 (2006)
[Non Patent Literature 7] *Proc. Natl. Acad. Sci. USA* 95, 10769-10773 (1998)
[Non Patent Literature 8] *Proc. Natl. Acad. Sci. USA* 98:6759-6764 (2001)
[Non Patent Literature 9] *Nature* 436, 221-226 (2005)
[Non Patent Literature 10] *Nucleic Acids Res.,* 31, 6873-6881 (2003)
[Non Patent Literature 11] *Nucleic Acids Res.,* 35, e87 (2007)
[Non Patent Literature 12] *Proc Natl. Acad. Sci. USA,* 103, 15008-15013 (2006)
[Non Patent Literature 13] *Biotech. Bioeng.* 89, 530-538 (2005)
[Non Patent Literature 14] *Journal of Immunological Methods* 295, 49-56 (2004)
[Non Patent Literature 15] *Metabolic Engineering* 9, 304-316 (2007)
[Non Patent Literature 16] *Gene* 199, 293-301 (1997)

DISCLOSURE OF INVENTION

Problems to be Solved by the Invention

In order to produce and analyze a protein of interest, it is necessary to select a cell line which stably and highly expresses a protein of interest, using a mammalian-derived culture cell. However, preparing and culturing the cell that produces the protein of interest require considerable effort and time.

In addition, though it is known that a protein is expressed in a mammalian cell using a transposon sequence, preparation of a cell highly expressing a protein and thus can be used as a protein production system by using a transposon sequence; a high production cell comprising a transposon sequence; and a production method of a protein using the cell are not known. Further, any example that a high expression cell can be obtained by modifying codon to suppress expression (translation) of a drug resistance gene is not known.

As described in the above, the expression of a protein of interest in a large amount by establishing a protein production system which can highly produce a protein of interest using a mammalian culture cell efficiently and within a short period has been required. In addition, establishment of a producing cell which does not require any components derived from an animal consistently, from the gene introduction to establishment of a producing cell, has been desired.

Thus, the objects of the present invention are to provide a cell capable of highly expressing a protein of interest which can be efficiently established, and a method for producing the protein of interest using the cell.

Means for Solving the Problems

To solve the above-mentioned problems, the present inventors have conducted intensive studies and found as a result that a production cell which highly expressing a protein of interest can be efficiently produced by introducing an expression vector which comprises a gene fragment comprising a DNA encoding the protein of interest and an attenuated selectable marker gene and also comprises a pair of transposon sequences at both terminals of the gene fragment, into a suspension mammalian cell; and integrating the gene fragment inserted between the pair of transposon sequences into a chromosome of the suspension mammalian cell. In addition, it was found that time for preparing a high expression cell line of the protein of interest could be drastically reduced, and thereby the invention was accomplished. Therefore, the object of the present invention is to provide a novel preparation method of a production cell which can efficiently prepare the production cell which highly expresses a exogenous gene; and a production method of a recombinant protein.

Specifically, the present invention relates to the followings:

1. A method for producing a protein of interest, comprising introducing an expression vector which comprises a gene fragment comprising a DNA encoding the protein of interest and an attenuated selectable marker gene and also comprises a pair of transposon sequences at both terminals of the gene fragment, into a suspension mammalian cell; integrating the gene fragment comprising the DNA encoding the protein of interest inserted between the pair of transposon sequences into a chromosome of the mammalian cell; obtaining a mammalian cell which expresses the protein of interest; and suspension-culturing the mammalian cell;

2. A method for producing a protein of interest, comprising the following steps (A) and (B):
(A) a step of simultaneously introducing the following expression vectors (a) and (b) into a suspension mammalian cell; integrating a gene fragment inserted between a pair of transposon sequences into a chromosome of the mammalian cell by a transiently expressed transposase; and obtaining a suspension mammalian cell which expresses the protein of interest:
(a) an expression vector which comprises the gene fragment comprising a DNA encoding the protein of interest and an attenuated selectable marker gene and also comprises the pair of transposon sequences at both terminals of the gene fragment,
(b) an expression vector which comprises a DNA encoding the transposase which recognizes the transposon sequences and has activity of transferring the gene fragment inserted between the pair of transposon sequences into the chromosome,
(B) a step of suspension-culturing the suspension mammalian cell which expresses the protein of interest to produce the protein of interest;

3. The method described in above item 1 or 2, wherein the suspension mammalian cell is a cell capable of surviving and proliferating in a serum-free medium;

4. The method described in any one of the above items 1 to 3, wherein the suspension mammalian cell is any one of the cells selected from a suspension CHO cell in which a CHO cell is adapted to suspension culture, a PER.C6 cell, a rat myeloma cell YB2/3HL.P2.G11.16Ag.20 (or also called YB2/0) and a suspension mouse myeloma cell NS0 adapted to suspension culture;

5. The method described in the above item 4, wherein the CHO cell is any one of the cells selected from CHO-K1, CHO-K1SV, DUKXB11, CHO/DG44, Pro-3 and CHO-S;

6. The method described in any one of the above items 1 to 5, wherein the attenuated selectable marker gene is a selectable marker gene modified such that expression level in the mammalian cell is lowered;

7. The method described in the above item 6, wherein the selectable marker gene modified such that expression level in the mammalian cell is lowered is a selectable marker gene modified to encode the same amino acid sequence as the selectable marker gene before the modification and to comprise codons used at a low frequency in the mammalian cell;

8. The method described in the above item 6 or 7, wherein the selectable marker gene modified such that expression level in the mammalian cell is lowered is modified in 10% or more of the nucleotide sequence encoding the selectable marker gene before the modification;

9. The method described in any one of the above items 6 to 8, wherein the selectable marker gene modified such that expression level in the mammalian cell is lowered is modified such that 70% or more of codons corresponding to leucine residue are TTA among the codons corresponding to leucine residue included in the gene;

10. The method described in any one of the above items 6 to 9, wherein the selectable marker gene modified such that expression level in the mammalian cell is lowered is modified such that 70% or more of codons corresponding to alanine residue are GCG among the codons corresponding to alanine residue included in the gene;

11. The method described in any one of the above items 6 to 10, wherein the selectable marker gene modified such that expression level in the mammalian cell is lowered is modified such that all the codons corresponding to leucine residue included in the gene are TTA or all the codons corresponding alanine residue included in the gene are GCG;

12. The method described in any one of the above items 1 to 11, wherein the selectable marker gene is one selectable marker gene selected from the group consisting of a neomycin resistance gene, a puromycin resistance gene, a hygromycin resistance gene, a zeocin resistance gene, and a blasticidin resistance gene;

13. The method described in any one of the above items 1 to 12, wherein the pair of transposon sequences are nucleotide sequences derived from a pair of transposons which function in a mammalian cell;

14. The method described in the above item 13, wherein the nucleotide sequences derived from the pair of transposons are nucleotide sequences derived from a pair of Tol2;

15. The method described in the above item 14, wherein the nucleotide sequences derived from the pair of Tol2 are the nucleotide sequence shown in SEQ ID NO:2 and the nucleotide sequence shown in SEQ ID NO:3;

16. The method described in the above item 13, wherein the nucleotide sequences derived from the pair of transposons are the nucleotide sequences shown in SEQ ID NO:35 and the nucleotide sequence shown in SEQ ID NO:36;

17. A suspension mammalian cell, in which an expression vector which comprises a gene fragment comprising a DNA encoding a protein of interest and an attenuated selectable marker gene and also comprises a pair of transposon sequences at both terminals of the gene fragment is introduced, and, wherein the gene fragment inserted between the pair of transposon sequences is integrated into a chromosome of the suspension mammalian cell, and the suspension mammalian cell produces the protein of interest;

18. A suspension mammalian cell, which has a chromosome into which a gene fragment inserted between a pair of transposons is integrated and which produces a protein of interest obtainable by simultaneously introducing the following vectors (a) and (b):

(a) a protein expression vector which comprises a gene fragment comprising a DNA encoding the protein of interest and an attenuated selectable marker gene and also comprises the pair of transposon sequences at both terminals of the gene fragment, (b) an expression vector which comprises a DNA encoding a transposase which recognizes the transposon sequences and has activity of transferring the gene fragment inserted between the pair of transposon sequences into the chromosome;

19. The mammalian cell described in the above item 17 or 18, which is a mammalian cell capable of surviving and proliferating in a serum-free medium;

20. The mammalian cell described in any one of the above items 17 to 19, wherein the cell is any one of the cells selected from a suspension CHO cell in which a CHO cell is adapted to suspension culture, a PER.C6 cell, a rat myeloma cell YB2/3HL.P2.G11.16Ag.20 (or also called YB2/0) and a suspension mouse myeloma cell NS0 adapted to suspension culture;

21. The mammalian cell described in the above item 20, wherein the CHO cell is any one of the cells selected from CHO-K1, CHO-K1SV, DUKXB11, CHO/DG44, Pro-3 and CHO-S;

22. The mammalian cell described in any one of the above items 17 to 21, wherein the attenuated selectable marker gene is a selectable marker gene modified such that expression level in the mammalian cell is lowered;

23. The mammalian cell described in the above item 22, wherein the selectable marker gene modified such that expression level in the mammalian cell is lowered is a selectable marker gene modified to encode the same amino acid sequence as the selectable marker gene before the modification and to comprise codons used at a low frequency in the mammalian cell;

24. The mammalian cell described in the above item 22 or 23, wherein the selectable marker gene modified such that expression level in the mammalian cell is lowered is modified in 10% or more of the nucleotide sequence encoding the selectable marker gene before the modification;

25. The mammalian cell described in any one of the above items 22 to 24,
wherein the selectable marker gene modified such that expression level in the mammalian cell is lowered is modified such that 70% or more of codons corresponding to leucine residue are TTA among the codons corresponding to leucine residue included in the gene;

26. The mammalian cell described in any one of the above items 22 to 25, wherein the selectable marker gene modified such that expression level in the mammalian cell is lowered is modified such that 70% or more of codons corresponding to alanine residue are GCG among the codons corresponding to alanine residue included in the gene;

27. The mammalian cell described in any one of the above items 22 to 26, wherein the selectable marker gene modified such that expression level in the mammalian cell is lowered is modified such that all the codons corresponding to leucine residue included in the gene are TTA or all the codons corresponding alanine residue included in the gene are GCG;

28. The mammalian cell described in any one of the above items 17 to 27, wherein the selectable marker gene is one selectable marker gene selected from the group consisting of a neomycin resistance gene, a puromycin resistance gene, a hygromycin resistance gene, a zeocin resistance gene, and a blasticidin resistance gene;

29. The mammalian cell described in any one of the above items 17 to 28, wherein the pair of transposon sequences are nucleotide sequences derived from a pair of transposons which function in a mammalian cell;

30. The mammalian cell described in the above item 29, wherein the nucleotide sequences derived from the pair of transposons are nucleotide sequences derived from a pair of Tol2;

31. The mammalian cell described in the above item 30, wherein the nucleotide sequences derived from the pair of Tol2 are the nucleotide sequence shown in SEQ ID NO: 2 and the nucleotide sequence shown in SEQ ID NO: 3;

32. The mammalian cell described in the above item 29, wherein the nucleotide sequences derived from the pair of transposons are the nucleotide sequences shown in SEQ ID NO:35 and the nucleotide sequence shown in SEQ ID NO:36;

33. An expression vector, which comprises a gene fragment comprising a DNA encoding a protein of interest and an attenuated selectable marker, and also comprises a pair of transposon sequences at both terminals of the gene fragment;

34. The expression vector described in the above item 33, wherein the pair of transposon sequences are nucleotide sequences derived from a pair of Tol2;

35. The expression vector described in the above item 34, wherein the nucleotide sequences derived from the pair of Tol2 are the nucleotide sequence shown in SEQ ID NO:2 and the nucleotide sequence shown in SEQ ID NO:3;

36. The vector described in any one of the above items 33 to 35, wherein the attenuated selectable marker gene is a selectable marker gene modified such that expression level in the mammalian cell is lowered;

37. The vector described in the above item 36, wherein the selectable marker gene modified such that expression level in the mammalian cell is lowered is a selectable marker gene modified to encode the same amino acid sequence as the selectable marker gene before the modification and to comprise codons used at a low frequency in the mammalian cell;

38. The vector described in the above item 36 or 37, wherein the selectable marker gene modified such that expression level in the mammalian cell is lowered is modified in 10% or more of the nucleotide sequence encoding the selectable marker gene before the modification;

39. The vector described in any one of the above items 36 to 38, wherein the selectable marker gene modified such that expression level in the mammalian cell is lowered is modified such that 70% or more of codons corresponding to leucine residue are TTA among the codons corresponding to leucine residue included in the gene;

40. The vector described in any one of the above items 36 to 39, wherein the selectable marker gene modified such that expression level in the mammalian cell is lowered is modified such that 70% or more of codons corresponding to alanine residue are GCG among the codons corresponding to alanine residue included in the gene;

41. The vector described in any one of the above items 36 to 40, wherein the selectable marker gene modified such that expression level in the mammalian cell is lowered is modified such that all the codons corresponding to leucine residue included in the gene are TTA or all the codons corresponding alanine residue included in the gene are GCG;

42. The vector described in any one of the above items 33 to 41, wherein the selectable marker gene is one selectable marker gene selected from the group consisting of a neomycin resistance gene, a puromycin resistance gene, a hygromycin resistance gene, a zeocin resistance gene, and a blasticidin resistance gene.

Effect of Invention

According to the protein production method of the present invention, a protein of interest can be efficiently produced by using a mammalian cell. The cell of the present invention can be used as a protein production cell for producing a recombinant protein.

BRIEF DESCRIPTION OF THE DRAWINGS

FIG. 1 shows structure of the antibody expression vector A. In FIG. 1, Tol2-L represents a DNA fragment comprising the Tol2-L sequence (SEQ ID NO:2), and Tol2-R represents a DNA fragment comprising the Tol2-R sequence (SEQ ID NO:3), CMV represents a CMV promoter, poly A represents a polyadenylation site, Hc represents a heavy chain gene of CD98 antibody, Lc represents an anti-human CD98 antibody light chain gene, SO represents an SV40 promoter, SV represents an SV40 polyadenylation site, and Neo-r represents a neomycin resistance gene.

EMBODIMENTS FOR CARRYING OUT THE INVENTION

The present invention relates to a method for producing a protein of interest, comprising introducing an expression vector which comprises a gene fragment comprising a DNA encoding the protein of interest and a selectable marker gene and also comprises a pair (two) of transposon sequences at both terminals of the gene fragment, into a suspension mammalian cell; integrating the gene fragment inserted between the pair of transposon sequences into a chromosome of the mammalian cell; obtaining a suspension mammalian cell producing the protein of interest; and suspension-culturing the mammalian cell, and a suspension mammalian cell which expresses the protein of interest by the method.

The examples of the cell producing a protein of interest of the present invention include a suspension mammalian cell, wherein an expression vector which comprises a gene fragment comprising a DNA encoding a protein of interest and a selectable marker gene and also comprises a pair of transposon sequences at both terminals of the gene fragment is introduced, the gene fragment inserted between the pair of transposon sequences is integrated into a chromosome, and the suspension mammalian cell produces the protein of interest.

Further, the examples of the cell producing a protein of interest of the present invention include a suspension mammalian cell, which has a chromosome into which a gene fragment inserted between a pair of transposons is integrated and which produces the protein of interest obtainable by simultaneously introducing the following vectors (a) and (b):

(a) an expression vector which comprises the gene fragment comprising a DNA encoding the protein of interest and a selectable marker gene and also comprises the pair of transposon sequences at both terminals of the gene fragment, (b) an expression vector which comprises a DNA encoding a transposase which recognizes the transposon sequences and has activity of transferring the gene fragment inserted between the pair of transposon sequences into the chromosome.

The examples of the method for producing a protein of interest of the present invention include a method for producing a protein of interest, comprising the following steps (A) and (B):

(A) a step of simultaneously introducing the following expression vectors (a) and (b) into a suspension mammalian cell and obtaining a suspension mammalian cell which expresses the protein of interest by integrating a gene fragment inserted between a pair of transposon sequences into a chromosome of the mammalian cell by a transiently expressed transposase:

(a) an expression vector which comprises the gene fragment comprising a DNA encoding the protein of interest and a selectable marker gene and also comprises the pair of transposon sequences at both terminals of the gene fragment, (b) an expression vector which comprises a DNA encoding the transposase which recognizes the transposon sequences and has activity of transferring the gene fragment inserted between the pair of transposon sequences into the chromosome, and (B) a step of suspension-culturing the suspension mammalian cell which expresses the protein of interest to produce the protein of interest.

The terms used in the present specification include the following definitions.

The term transposon is a transposable genetic element and means a gene unit which moves on a chromosome or from a chromosome to another chromosome (transposition) while keeping a certain structure.

The transposon has a repeating transposon sequences (also called inverted repeat sequence (IR sequence) or terminal inverted repeat sequence (TIR sequence)) which positions in the same direction or the reverse direction at both terminals of a gene unit and a nucleotide sequence encoding a transposase which recognizes the transposon sequence to introduce a gene existing between the transposon sequences.

The transposase translated from the transposon can introduce a DNA by recognizing transposon sequences of both terminals of the transposon, cleaving out the DNA fragment inserted between the pair of transposon sequences and inserting the fragment into the site to be introduced.

The term transposon sequence means the nucleotide sequence of a transposon recognized by a transposase and has the same meaning as the IR sequence or TIR sequence. The sequence may comprise an imperfect repeating moiety as long as it can be introduced (inserted into other position in the genome) by the activity of a transposase, and there is a transposon sequence specific to a transposase.

The transposon sequence to be used in the present invention may be any sequence as long as it is a nucleotide sequence derived from natural or artificial transposons which can be recognized by a transposase and be transposed in mammalian cells. Examples thereof include the medaka fish-derived Tol1 and Tol2 transposons, the Sleeping Beauty reconstructed from a non-autonomous transposon existed in an *Onchorhynchus* fish genome, the frog-derived artificial transposon Frog Prince and the insect-derived transposon PiggyBac.

Particularly, among them, the nucleotide sequences derived from the medaka fish-derived Tol2 transposon comprising the nucleotide sequence shown in SEQ ID NO:6 is preferable. As the nucleotide sequence derived from a pair of Tol2 transposons, examples include the nucleotide sequence comprising a nucleotide sequence at positions 1 to 2229 and the nucleotide sequence at positions the 4148 to 4682 in the Tol2 transposon nucleotide sequence shown in SEQ ID NO:6 of Sequence Listing.

As the nucleotide sequence derived from a pair of Tol2 transposons, the nucleotide sequence at positions 1 to 200 (SEQ ID NO:2) (hereinafter referred to as "Tol2-L sequence") and the nucleotide sequence at positions 2285 to 2788 (SEQ ID NO:3) (hereinafter referred to as "Tol2-R sequence") in the Tol2 transposon nucleotide sequence shown in SEQ ID NO:1 of Sequence Listing are more preferable.

As the transposon sequence of the present invention, the nucleotide sequence derived from the medaka fish-derived Tol1 transposon consisting of the nucleotide sequence shown in SEQ ID NO:37 of Sequence Listing can be used. As the nucleotide sequence derived from a pair of Tol1 transposons, examples include a nucleotide sequence at positions 1 to 157 and a nucleotide sequence at positions 1748 to 1855 in the nucleotide sequence derived from the medaka fish-derived Tol1 transposon consisting of the nucleotide sequence shown in SEQ ID NO:37 of Sequence Listing.

As the nucleotide sequence derived from a pair of Tol1 transposons, the region at positions 1 to 200 (SEQ ID NO:35) (hereinafter referred to as "Tol1-L sequence") and the region at positions 1351 to 1855 (SEQ ID NO:36) (hereinafter referred to as "Tol1-R sequence") in the nucleotide sequence derived from Tol1 transposon consisting of the nucleotide sequence shown in SEQ ID NO:37 of Sequence Listing are more preferable.

Examples of the transposon sequence of the present invention include transposon sequences of which transposition reactions are controlled by using a partial sequence of a transposon sequence specific to the above-mentioned transposon, by adjusting the length of the nucleotide sequence and by modifying the nucleotide sequence due to addition, deletion or substitution. Regarding the control of the transposition reaction of a transposon, the transposition reaction can either be accelerated or suppressed by raising or lowering recognition of the transposon sequence by a transposase, respectively.

The term transposase means an enzyme which recognizes nucleotide sequences having transposon sequences and transfers a gene fragment existing between the nucleotide sequences on a chromosome or from the chromosome to another chromosome.

Examples of the transposase include enzymes derived from Tol1 and Tol2 which are derived from medaka fish, the Sleeping Beauty reconstructed from a non-autonomous transposon existed in an *Onchorhynchus* fish genome, the artificial transposon Frog prince which is derived from frog and the transposon PiggyBac which is derived from insect.

As the transposase, a native enzyme may be used, and any transposase in which a part of its amino acids are substituted, deleted, inserted and/or added may be used as long as the same transposition activity as the transposase is maintained. By controlling the enzyme activity of the transposase, the transposition reaction of the DNA existing between the transposon sequences can be controlled.

In order to analyze whether or not it possesses a transposition activity similar to that of transposase, it can be measured by the 2-components analyzing system disclosed in Japanese Published Unexamined Patent Application No. 2003-235575. Particularly, whether or not a non-autonomous Tol2 element can be transferred and inserted into a mammalian cell chromosome by the activity of a transposase can be analyzed by separately using a plasmid comprising a Tol2 transposase-deleted Tol2 transposon (Tol2-derived non-autonomous transposon) and a plasmid comprising Tol2 transposase.

The term non-autonomous transposon in the present invention means a transposon which is lost a transposase existed inside the transposon and can not therefore perform its autonomous transposition. The non-autonomous transposon can transfer the DNA inserted between transposon sequences of the non-autonomous transposon into the host cell chromosome, by allowing a transposase protein, an mRNA encoding the transposase protein or a DNA encoding the transposase protein to simultaneously present in the cell.

The transposase gene means a gene encoding a transposase. In order to improve its expression efficiency in a mammalian cell, a sequence which adjusts a space between the Kozak's consensus sequence (Kozak M., *Nucleic Acids Res.*, 12, 857-872 (1984)) or a ribosome binding sequence, Shine-Dalgarno sequence and the initiation codon, to an appropriate distance (e.g., from 6 to 18 bases) may be connected to an upstream site of the translation initiation codon ATG of the gene.

According to the present invention, in order to integrate an expression vector into the chromosome of a host cell, a transposase is allowed to act upon the expression vector. In order to allow a transposase to act upon a cell, the transposase enzyme may be injected into the cell, or a DNA encoding transposase gene may be introduced into an intended expression vector and the vector may be transfected with the cell. In addition, by transfecting with an RNA encoding a transposase gene into the cell, the transposase may be expressed in the cell.

The expression vector which can be used herein is not particularly limited. Any expression vector can be used by optionally selecting from the expression vectors known to those skilled in the art, depending on a host cell into which an expression vector comprising a transposase gene is introduced; the use; and the like.

In the case where a protein of interest comprised of two or more polypeptides is produced by the method of the present invention, the expression vector may be integrated into a chromosome of a host cell by inserting the DNA encoding each of two or more polypeptides on the same or different expression vector. Specifically, a heavy chain and a light chain of an antibody may be inserted into different expression vectors and the expression vector may be integrated into a chromosome of a host cell.

The transposase may be inserted into an expression vector to express together with the protein of interest or may be inserted into a vector different from the expression vector. The transposase may be allowed to act transiently or may be allowed to act continuously, but it is preferably to allow the transposase to act transiently in order to prepare a cell for stable production.

In order to allow the transposase to act transiently, for example, a transposase gene may be inserted into an expression plasmid which is different from an expression vector having a protein of interest and a cell may be transfected with them.

The term expression vector means an expression vector to be used for introducing into a mammalian cell. The expression vector used in the present invention has a structure in which at least a pair of transposon sequences is present at both sides of an expression cassette.

The term expression cassette means a nucleotide sequence which has a gene expression controlling region necessary for expressing a protein of interest and a sequence encoding the protein of interest. Examples of the gene expression controlling region include an enhancer, a promoter, and a terminator. The expression cassette may include a selectable marker gene.

Any promoter can be used, so long as it can function in an animal cell. Examples include a promoter of IE (immediate early) gene of cytomegalovirus (CMV), SV40 early promoter, a promoter of retrovirus, a metallothionein promoter, a heat shock promoter, SRα promoter, moloney murine leukemia virus, an enhancer and the like. Also, the enhancer of the IE gene of human CMV can be used together with the promoter.

The selectable marker gene means an optional marker gene which can be used for distinguishing a cell to which a plasmid vector is introduced from a cell lacking of the vector. Examples of the selectable marker gene include a drug resistance gene (such as a neomycin resistance gene, DHFR gene, a puromycin resistance gene, a blasticidin resistance gene, a zeocin resistance gene, and a hygromycin resistance gene), fluorescence and bio-luminescence marker genes (such as green fluorescent protein GFP) and the like.

An attenuated selectable marker gene is a selectable marker gene which is modified in such a manner that activity of the protein encoded by the selectable marker gene inside the cell is lowered.

Examples of the selectable marker gene which is modified in such a manner that the activity in the cell becomes low include (A) an selectable marker gene in which an amino acid sequence of a protein encoded by a selectable marker gene is modified so that activity of the protein in the cell is lowered or (B) an selectable marker gene in which a nucleotide sequence which controls expression of a selectable marker gene is modified or a nucleotide sequence inside of ORF (open reading frame) is modified so that the expression of the selectable marker gene is lowered.

Examples of the selectable marker gene in which an amino acid sequence of a protein encoded by a selectable marker gene is modified so that activity of the protein in the cell is lowered include the neomycin resistance gene described by Sauter et al. [*Biotech. Bioeng.*, 89, 530-538 (2005)] or Chen et al. [*Journal of Immunological Methods*, 295, 49-56 (2004)].

Examples of the method for lowering expression level of a protein in the cell by modifying a nucleotide sequence which controls expression of the selectable marker gene include a method for modifying the sequence of promoter sequence, terminator sequence, enhancer sequence, kozak's consensus sequence or Shine-Dalgarno sequence, which controls expression of the selectable marker gene.

More specifically, examples include a method in which a promoter sequence which controls expression of a selectable marker gene is replaced by a weaker promoter sequence.

Examples of the method for lowering expression level of the protein in the cell by modifying a nucleotide sequence in the ORF of a selectable marker gene include a method in which a codon in the ORF is replaced by a synonymous codon having further lower frequency of codon usage in the cell.

Examples of the attenuated selectable marker gene of the present invention include a selectable marker in which the above codon in the ORF of the gene is replaced by a synonymous codon having further lower frequency of codon usage in the cell.

In the cells of various biological species, the synonymous codon having further lower frequency of usage among each synonymous codon can be selected based on known literatures, data bases and the like.

As such a replacement by a synonymous codon having lower frequency of usage, specifically in the case of CHO cell, examples include replacement of the codon of leucine with TTA, replacement of the codon of arginine with CGA or CGT, replacement of the codon of alanine with GCG, replacement of the codon of valine with GTA, replacement of the codon of serine with TCG, replacement of the codon of isoleucine with ATA, replacement of the codon of threonine with ACG, replacement of the codon of proline with CCG, replacement of the codon of glutamic acid with GAA, replacement of the codon of tyrosine with TAT, replacement of the codon of lysine with AAA, replacement of the codon of phenylalanine with TTT, replacement of the codon of histidine with CAT, replacement of the codon of glutamine with CAA, replacement of the codon of asparagine with AAT, replacement of the codon of aspartic acid with GAT, replacement of the codon of cysteine with TGT and replacement of the codon of glycine with GGT.

In an attenuated selectable marker gene, the number of codons to be placed compared to the selectable marker gene before the modification is not particularly limited as long as a protein producing cell can be efficiently obtained, but it is preferable to replace codons corresponding to 20 or more amino acid residues.

In an attenuated selectable marker gene, the number of bases to be modified compared to the selectable marker gene before modification is not particularly limited, but it is preferable to modify 10% or more of the nucleotide sequence encoding the selectable marker gene.

In addition, in an attenuated selectable marker gene, the amino acid residues encoded by the codons to be replaced is not particularly limited, but preferable examples include leucine, alanine, serine and valine.

In the case of an attenuated selectable marker gene, in the case where the codons corresponding to leucine are replaced not particularly limited, but it is preferable to replace the codons corresponding to 70% or more of leucine residues among the codons corresponding to the total of the leucine residues contained in the selectable marker gene. Also, in the case of an attenuated selectable marker gene, when the codons corresponding to alanine are replaced not particularly limited, but it is preferable to replace the codons corresponding to 70% or more of alanine residues among the codons corresponding to the total of the alanine residues contained in the selectable marker gene.

Specific examples of the attenuated selectable marker gene obtained by such as a modification in which codons are replaced with synonymous codons having lower frequency of usage include a neomycin resistance gene comprising the nucleotide sequence represented by SEQ ID NO:9, 11 or 13, a puromycin resistance gene comprising the nucleotide sequence represented by SEQ ID NO:21, 23 or 25, a Zeocin resistance gene consisting of the nucleotide sequence represented by SEQ ID NO:27 or 29 and a hygromycin resistance gene comprising the nucleotide sequence represented by SEQ ID NO:31 or 33.

In addition, it is possible to attenuate a selectable marker gene also by considerably increasing concentration of a drug in comparison with the conventionally used concentration when a drug-resistant cell is selected in preparing an antibody producing cell or by carrying out additional administration before the drug resistance gene metabolizes and degrades the drug.

The method for introducing the above-mentioned expression vector comprising a transposon sequence, a plasmid vector for expressing a transposase or RNA is not particularly limited. Examples include calcium phosphate transfection, electroporation, a liposome method, a gene gun method, lipofection and the like. Examples of the method for directly introducing a transposase in the form of a protein include a microinjection technique or supply into a cell by endocytosis. The gene introduction can be carried out by the method described in Shin Idenshi Kogaku Handbook (New Genetic Engineering Handbook), edited by Masami Muramatsu and Tadashi Yamamoto, published by Yodo-sha, ISBN 9784897063737.

The host cell may be any mammalian cell as long as it can be subcultured and stably express a protein of interest.

Examples of the particular host cell include PER.C6 cell, human leukemia cell Namalwa cell, monkey cell COS cell, rat myeloma cell YB2/3HL.P2.G11.16Ag.20 (also referred to as YB2/0), mouse myeloma cell NS0, mouse myeloma cell SP2/0-Ag14, Syrian hamster cell BHK, HBT5637 (Japanese Unexamined Patent Application Publication No. 1998-000299), Chinese hamster ovarian cell CHO cell (*Journal of Experimental Medicine*, 108, 945 (1958); *Proc. Natl. Acad. Sci. USA.*, 601275 (1968); *Genetics*, 55, 513 (1968); *Chromosoma*, 41, 129 (1973); *Methods in Cell Science*, 18, 115 (1996); *Radiation Research*, 148, 260 (1997); *Proc. Natl. Acad. Sci. USA.*, 77, 4216 (1980); *Proc. Natl. Acad. Sci.*, 60, 1275 (1968); *Cell*, 6, 121 (1975); *Molecular Cell Genetics, Appendix I,II* (pp. 883-900)), CHO/DG44 (ATCC CRL-9096), CHO-K1 (ATCC CCL-61), DUKXB11 (ATCC CCL-9096), Pro-5 (ATCC CCL-1781), CHO-S (Life Technologies, Cat #11619), Pro-3 and subline cell line of CHO cell.

In addition, the above-mentioned host cell can also be used in the protein production method of the present invention by modifying the cell so as to be suitable for the protein production, due to modification of chromosomal DNA, introduction of an exogenous gene, and the like.

Further, in the present invention, in order to control the sugar chain structure bound to a protein of interest to be produced, Lec13 which acquired lectin resistance [*Somatic Cell and Molecular Genetics*, 12, 55 (1986)] or a CHO cell from which α-1,6-fucosyltransferase gene is deleted (WO2005/35586, WO2002/31140), can also be used as the host cell producing a protein of interest of the present invention.

The protein of interest produced in the present invention may be any protein as long as it can be expressed by the method of producing a protein using a non-autonomous transposon of the present invention. Particularly, examples of the protein of interest include a human serum protein, a peptide hormone, a growth factor, a cytokine, a blood coagulation factor, a fibrinolytic protein, an antibody partial fragments of various proteins and the like.

Examples of the protein of interest produced in the present invention include preferably a monoclonal antibody such as a chimeric antibody, a humanized antibody, and a human antibody, a Fc fusion protein, an albumin binding protein and a partial fragment thereof.

The effector activity of a monoclonal antibody produced in the present invention can be controlled by various methods. Examples of the known methods include a method for controlling an amount of fucose (hereinafter, referred to also as "core fucose") which is bound N-acetylglucosamine (GlcNAc) through α-1,6 bond in a reducing end of a complex type N-linked sugar chain which is bound to asparagine (Asn) at position 297 of an Fc region of an antibody (WO 2005/035586, WO 2002/31140, and WO 00/61739), a method for controlling an effector activity by modifying amino acid residue(s) of an Fc region of the antibody, or the like. The effector activity of the monoclonal antibody produced in the present invention can be controlled by using any of the methods.

The effector activity means an antibody-dependent activity which is induced via an Fc region of an antibody. As the effector activity, an antibody-dependent cellular cytotoxicity (ADCC activity), a complement-dependent cytotoxicity (CDC activity), an antibody-dependent phagocytosis (ADP activity) by phagocytic cells such as macrophages or dendritic cells, and the like are known.

In addition, by controlling a content of core fucose of a complex type N-linked sugar chain of Fc of a monoclonal antibody which is produced in the present invention, an effector activity of the antibody can be increased or decreased. As a method for lowering a content of fucose which is bound to a complex type N-linked sugar chain bound to Fc of the antibody, an antibody to which fucose is not bound can be obtained by the expression of an antibody using a CHO cell which is deficient in a gene encoding α-1,6-fucosyltransferase.

The antibody to which fucose is not bound has a high ADCC activity. On the other hand, as a method for increasing a content of fucose which is bound to a complex type N-linked sugar chain bound to Fc of an antibody, an antibody to which fucose is bound can be obtained by the expression of an antibody using a host cell into which a gene encoding α-1,6-fucosyltransferase is introduced. The antibody to which fucose is bound has a lower ADCC activity than the antibody to which fucose is not bound.

Further, by modifying amino acid residue(s) in an Fc region of an antibody, the ADCC activity or CDC activity can be increased or decreased. For example, the CDC activity of an antibody can be increased by using the amino acid sequence of the Fc region described in US 2007/0148165. Further, the ADCC activity or CDC activity can be increased or decreased by carrying out amino acid modification described in U.S. Pat. Nos. 6,737,056, or 7,297,775 or 7,317,091.

The term suspension mammalian cell in the present invention means a cell which does not adhere to a cell culture anchorage coated for facilitating adhesion of culture cells, such as microbeads, a culture container for tissue culture (also referred to as a tissue culture or adhesion culture container and the like) and the like, and can survive and grow while suspending in the culture solution. As long as the cell does not adhere to the cell culture anchorage, the cell may survive and grow in a state of a single cell in the culture solution or survive and grow in a state of a mass of cells formed by the agglutination of two or more cells.

In addition, as the suspension mammalian cell to be used in the present invention, a cell which can survive and grow in a serum-free medium that does not contain fetal calf serum (hereinafter referred to as FCS) and the like, while suspending in the culture solution without adhering to the cell culture anchorage, is preferable, and a mammalian cell which can survive and grow while suspending in a protein-free medium that does not contain protein is more preferable.

The culture container for tissue culture may be any one such as a flask, a Petri dish and the like as long as it is coated for adhesion culture is applied thereto. Particularly, whether or not it is a suspension mammalian cell can be confirmed using commercially available tissue culture flask (manufactured by Greiner), adhesion culture flask (manufactured by Sumitomo Bakelite) and the like.

As the suspension mammalian cell to be used in the present invention, it may be either a cell prepared by further adapting a cell originally having a suspension property to suspension culture or a suspension mammalian cell prepared by adapting an adhesive mammalian cell to suspension culture conditions. Examples of the cell originally having a suspension property include PER.C6 cell, a rat myeloma cell YB2/3HL.P2.G11.16Ag.20 (or also called YB2/0), CHO-S cell (manufactured by Invitrogen) and the like.

The suspension mammalian cell prepared by adapting an adhesive mammalian cell to suspension culture conditions in the present invention can be prepared by the method described in *Mol. Biotechnol.*, 2000, 15(3), 249-57 or by the method shown in the following, and can be prepared by establishing a cell which shows proliferation property and surviving property similar to those before adapting the suspension culture or superior to those before adapting to suspension culture (*J. Biotechnol.*, 2007, 130(3), 282-90).

The term similar to those before the suspension culture adaptation means that survival ratio, proliferation rate (doubling time) and the like of the cell adapted to the suspension culture are substantially the same as those of the cell before adapting suspension culture.

In the present invention, examples of the method for adapting an adhesive mammalian cell to suspension culture conditions include the following method. The serum content of a serum-containing medium is reduced to 1/10 and sub-culturing is repeated at relatively high concentration of cell. When the mammalian cell comes to be able to survive and proliferate, the serum content is further reduced and the sub-culturing is repeated. By this method, a suspension mammalian cell which can survive and proliferate under serum-free conditions can be prepared.

In addition, a suspension mammalian cell can also be prepared by culturing with the addition of an appropriate non-ionic surfactant such as Pluronic-F68 or the like in the culture solution. Examples of the suspension mammalian cell in which the adhesive mammalian cell is adapted to a suspension culture condition include a mouse myeloma cell NS0, a CHO cell or the like.

In the present invention, the suspension CHO cell preferably possesses a property that when suspension culturing is carried out under the condition of $2 \times 10^5$ cells/ml, the cell concentration after culturing for 3 or 4 days is preferably $5 \times 10^5$ cells/ml or more, more preferably $8 \times 10^5$ cells/ml or more, particularly preferably $1 \times 10^6$ cells/ml or more, most preferably $1.5 \times 10^6$ cells/ml or more. In addition, doubling time of the suspension CHO cell of the present invention is preferably 48 hours or less, more preferably 24 hours or less, particularly preferably 18 hours or less, most preferably 11 hours or less.

Examples of the medium for suspension culturing include commercially available medium, such as CD OptiCHO medium (Invitrogen), EX-CELL 325-PF medium (SAFC Biosciences), SFM4CHO medium (HyClone) and the like. In addition, it can also be obtained by mixing saccharides, amino acids, vitamins metal salts and the like which are necessary for the culturing of CHO cells.

The suspension culturing can be conducted by using a culture container which can be used for suspension culturing under a culture condition capable of suspension culturing. Examples of the culture container include a 96-well plate for suspension cell culture (manufactured by Corning), a T-flask (manufactured by Becton Dickinson), a conical flask (manufactured by Corning) and the like.

Regarding the culture conditions, for example, it can be statically cultured in an atmosphere of 5% $CO_2$ at a culture temperature of 37° C. A shaking culture equipment, such as culturing equipment for suspension culture exclusive use, e.g., Wave Bioreactor (manufactured by GE Healthcare Bioscience), can be also used.

Regarding the suspension culture conditions for a CHO cell using the Wave Bioreactor equipment, the cell can be cultured by the method described on the GE Healthcare Bioscience homepage http://www.gelifesciences.co.jp/tech_support/manual/pdf/cellcult/wave_03_16.pdf.

In addition to the shaking culture, culturing by a rotation agitation equipment such as a bioreactor, can also be used. Culturing using a bioreactor can be carried out by the method described in *Cytotechnology*, (2006) 52: 199-207, and the like.

In the present invention, when a cell line other than the CHO cells is selected, any cell line can be applied so long as it is a cell line adapted to the suspension culture by the above-mentioned method and the protein production method of the present invention can be used.

Purification of the protein produced by the cultured cell is carried out by separating the protein of interest from impurities other than the protein of interest in a culture solution or cell homogenate containing the protein. Examples of the separation method include centrifugation, dialysis, ammonium sulfate precipitation, column chromatography, a filtering or the like. The separation can be carried out based on the difference in physicochemical properties of the protein of interest and impurities or the difference in their avidity for the column carrier itself.

As the method for purifying the protein, the purification is carried out by the method described in *Protein Experimentation Note* (the first volume)—*Extraction, Separation and Expression of Recombinant Protein* (translation of a textbook written in Japanese) (edited by Masato Okada and Kaori Miyazaki, published by Yodo-sha, ISBN 9784897069180) and the like.

The entire contents of the references, such as the scientific documents, patents, patent applications cited herein are incorporated herein by reference to the same degree of those illustratively described, respectively.

The present invention has been described in the above by showing preferred embodiments thereof for the sake of easy understanding. Hereinafter, the present invention is described based on examples, but the above-mentioned explanations and the following examples are provided merely for the purpose of exemplifications and not provided for the purpose of limiting the invention. Accordingly, the scope of the present invention is not limited to the embodiments and examples which are specifically described in the present specification, but is limited by the claims alone.

Hereinafter, examples are shown to further describe the present specification specifically, but the present invention is not limited to the description of these examples.

Various experimental techniques relating to recombination described in the followings, such as the cloning and the like were carried out in accordance with the genetic engineering techniques described in *Molecular Cloning* $2^{nd}$ edition edited by J. Sambrook, E. F. Frisch and T. Maniatis, *Current Protocols in Molecular Biology* edited by Frederick M. Ausubel et al, published by Current Protocols, and the like.

EXAMPLES

Example 1

Preparation of a Transposon Vector which Expresses Neomycin Resistance Gene and Anti-Human CD98 Antibody (1) Preparation of a Transposon Vector which Expresses Wild Type Neomycin Resistance Gene and Anti-Human CD98 Antibody A plasmid which comprised a gene expression cassette for mammalian cell use comprising an arbitrary human antibody gene and a drug resistance marker gene inserted between a pair of Tol2-derived nucleotide sequences was used as the plasmid vector for protein expression.

The DNA of the gene to be used was obtained by carrying out chemical synthesis in the artificial way based on a conventionally known nucleotide sequence or by preparing primers of its both terminal sequences and thereby carrying out PCR using an appropriate DNA source. For the sake of the latter gene manipulations, a restriction enzyme digestion site was added to the primer terminal. In the non-autonomous Tol2 transposon nucleotide sequence (SEQ ID NO:1) disclosed by JP-A-2003-235575, a nucleotide sequence at positions 1 to 200 (Tol2-L sequence) (SEQ ID NO:2) and a nucleotide sequence at positions 2285 to 2788 (Tol2-R sequence) (SEQ ID NO:3) were used as the transposon sequences.

A DNA fragment comprising either of the Tol2-R sequence and Tol2-L sequence was synthesized.

A DNA fragment including a nucleotide sequence (SEQ ID NO:15) which encodes antibody H chain under control of CMV promoter, amplified based on the anti-human CD98 antibody N5KG1-Val C2IgG1NS/I117L vector (Japanese Patent No. 4324637), was prepared as the antibody heavy chain gene cassette, and a DNA fragment comprising a nucleotide sequence (SEQ ID NO:17) which encoded antibody light chain under control of SV40 promoter, amplified based on the anti-human CD98 antibody N5KG1-Val C2IgG1NS/I117L vector, as the antibody light chain gene cassette.

As the neomycin resistance gene cassette, a DNA fragment comprising a DNA which comprises a nucleotide sequence encoding a neomycin resistance gene under control of SV40 promoter (a DNA which encodes a neomycin phosphotransferase consisting of the nucleotide sequence represented by SEQ ID NO:7 and GenBank Accession No. U47120.2) was prepared.

An anti-CD98 antibody expression vector A was prepared by connecting the above-mentioned antibody heavy chain gene expression cassette, antibody light chain gene expression cassette and neomycin resistance gene expression cassette and further connecting its both terminals with a DNA fragment comprising a Tol2-R sequence and a DNA fragment comprising a Tol2-L sequence (FIG. 1).

(2) Preparation of Anti-Human CD98 Antibody Expression Transposon Vector Comprising a Modified Type Neomycin Resistance Gene 1

An anti-human CD98 antibody expression transposon vector B in which the neomycin resistance gene of the anti-human CD98 antibody expression transposon vector A obtained in (1) which comprises a wild type neomycin resistance gene was replaced by a modified type neomycin resistance gene 1 comprising the nucleotide sequence represented by SEQ ID NO:9 was prepared.

The modified type neomycin resistance gene 1 encodes an amino acid sequence identical to that of the wild type neomycin resistance gene and was modified to have a nucleotide sequence in which 167 bases corresponding to 22% of the entire were modified. Specifically, among the total of 32 leucine residues, codons corresponding to 25 leucine residues were modified so as to be TTA.

(3) Preparation of Anti-Human CD98 Antibody Expression Transposon Vector Comprising a Modified Type Neomycin Resistance Gene 2

An anti-human CD98 antibody expression transposon vector C in which the neomycin resistance gene of the anti-human CD98 antibody expression transposon vector A obtained in (1) which comprises a wild type neomycin resistance gene was replaced by a modified type neomycin resistance gene 2 comprising the nucleotide sequence represented by SEQ ID NO:11 was prepared.

The modified type neomycin resistance gene 2 encoded the amino acid sequence identical to that of the wild type neomycin resistance gene and had a nucleotide sequence in which the 180 bases corresponding to 23% of the entire were modified. Specifically, among the total of 32 leucine residues, codons corresponding to 28 leucine residues were modified so as to be TTA.

(4) Preparation of Anti-Human CD98 Antibody Expression Transposon Vector Having a Modified Type Neomycin Resistance Gene 3

An anti-human CD98 antibody expression transposon vector D in which the neomycin resistance gene of the anti-human CD98 antibody expression transposon vector A obtained in (1) which comprises a wild type neomycin resistance gene was replaced by a modified type neomycin resistance gene 3 comprising the nucleotide sequence represented by SEQ ID NO:13 was prepared.

The modified type neomycin resistance gene 3 encoded the amino acid sequence identical to that of the wild type neomycin resistance gene and had a nucleotide sequence in which 203 bases corresponding to 26% of the entire were modified. Specifically, among the total of 32 leucine residues, codons corresponding to 30 leucine residues were modified so as to be TTA.

Example 2

Antibody production by antibody producer CHO cells which expresses modified type neomycin resistance gene Antibody producing cells A to D were prepared by introducing each of the anti-human CD98 expression transposon vectors A to D prepared in Example 1(1) to (4) into the suspension CHO-K1 cell together with a vector pCAGGS-T2TP which expresses a Tol2 transposase comprising the amino acid sequence represented by SEQ ID NO:5 [Kawakami K. & Noda T., *Genetics*, 166, 895 - 899 (2004)].

Introduction of vectors into the suspension CHO cell was carried out by suspending the CHO cell ($4 \times 10^6$ cells) in 400 µl of PBS buffer and co-transfecting the anti-human CD98 antibody expression transposon vector (10 µg) and Tol2 transposase expression vector pCAGGS-T2TP (20 µg) directly in the form of circular DNA by electroporation.

In this case, the Tol2 transposase expression vector was also introduced directly as circular DNA in order to transiently express Tol2 transposase.

In addition, as a control which did not use Tol2 transposase, the anti-human CD98 antibody expression transposon vector D (10 µg) of Example 1(4) was linearized using a restriction enzyme PciI (TAKARA BIO INC.) and then introduced into suspension CHO-K1 cell by electroporation.

The electroporation was carried out using an electroporator [Gene Pulser Xcell system (manufactured by Bio-Rad)] under conditions of voltage of 300 V, electrostatic capacity of 500 µF and room temperature and using a cuvette of 4 mm in gap width (manufactured by Bio-Rad).

After the gene introduction by electroporation, the cells in each cuvette were inoculated onto one 96-well plate and cultured for 3 days in a $CO_2$ incubator using a CD OptiCHO medium (Invitrogen) supplemented with 5% soybean hydrolyzate.

Next, from the medium exchange after 4 days of the gene introduction, culturing was carried out in the presence of G418 (Geneticin(R), Invitrogen) by adding the G418 to give a final concentration of 500 µg/ml, and the culturing was carried out for 3 weeks while changing the medium at intervals of one week.

After the culturing, expression of the antibody was determined using LANCE(R) assay (Perkin-Elmer Corp) by a sandwich method to which FRET (fluorescence resonance energy introduction) was applied. The results are shown in Table 1.

TABLE 1

|  | Antibody producing cells | | | | |
| --- | --- | --- | --- | --- | --- |
|  | A (Wild Type) | B (Modified Type 1) | C (Modified Type 2) | D (Modified Type 3) | Control cell |
| Antibody expression level (mg/L) of cells showing maximum expression | 0.5 | 2.0 | 1.6 | 5.1 | — |
| Average antibody expression level (mg/L) of top 10 cells | 0.5 | 0.7 | 0.7 | 1.7 | — |

As shown in Table 1, expression levels of anti-human CD98 antibody of the cells B to D expressing the modified type neomycin resistance genes were higher than that of the cell A which expressed the wild type neomycin resistance gene.

Particularly, in the case of the anti-human CD98 antibody producing cell D which expresses the modified type neomycin resistance gene 3, the cell line showing the times higher expression level than that of the anti-human CD98 antibody producing cell A which expresses the wild type neomycin resistance gene was obtained.

In addition, even when the modified type neomycin resistance gene 3 was used, it was not able to obtain a cell which expresses the anti-human CD98 antibody by the control cell into which the Tol2 transposase expression vector was not co-transfected in spite of making the vector into linear form.

Example 3

Preparation of Transposon Vector Expressing Puromycin Resistance Gene and Anti-Human CD98 Antibody (1) Preparation of Anti-Human CD98 Antibody Expression Transposon Vector Comprising Modified Type Puromycin Resistance Gene 1

An anti-human CD98 antibody expression transposon vector E in which the neomycin resistance gene of the anti-human CD98 antibody expression transposon vector A obtained in Example 1(1) which comprised wild type neomycin resistance gene, was replaced by a modified type puromycin resistance gene 1 consisting of the nucleotide sequence represented by SEQ ID NO:21 was prepared.

The modified type puromycin resistance gene 1 encoded an amino acid sequence identical to that of the wild type puromycin resistance gene consisting of the nucleotide sequence represented by SEQ ID NO:19 (a puromycin-N-acetyltransferase gene, consists of the nucleotide sequence disclosed in GenBank Accession No. U07648.1) and had a nucleotide sequence in which 17 bases corresponding to the 3% of the entire bases are modified.

Specifically, among the total of 28 alanine residues contained in the puromycin resistance gene, codons corresponding to 17 alanine residues were changed to GCG by the modification and, together with the codons which were already GCG in the wild type, the codons which correspond to all of the alanine residues were changed to GCG.

(2) Preparation of Anti-Human CD98 Antibody Expression Transposon Vector Comprising Modified Type Puromycin Resistance Gene 2

An anti-human CD98 antibody expression transposon vector F in which the neomycin resistance gene of the anti-human CD98 antibody expression transposon vector A obtained in Example 1(1) which comprises wild type neomycin resistance gene was replaced by a modified type puromycin resistance gene 2 comprising the nucleotide sequence represented by SEQ ID NO:23 was prepared.

The modified type puromycin resistance gene 2 encodes an amino acid sequence identical to that of the wild type puromycin resistance gene and had a nucleotide sequence in which 79 bases corresponding to the 14% of the entire bases are modified. Specifically, in addition to the modification of codons which correspond to the alanine residues of the modified type puromycin resistance gene 1, the codons corresponding to leucine residues were changed so as to be TTA, and the codons corresponding to valine residues were changed so as to be GTA and the codon of serine were changed so as to be TCG.

Example 4

Antibody Production by Antibody Producing CHO Cell which Expresses Modified Type Puromycin Resistance Gene 1

Antibody producing cells E and F were prepared by introducing the anti-human CD98 antibody expression transposon vector E of Example 3(1) comprising the modified type puromycin resistance gene 1, the anti-human CD98 antibody expression transposon vector F of Example 3(2) comprising the modified type puromycin resistance gene 2 and the Tol2 transposase expression vector pCAGGS-T2TP into the suspension CHO-K1 cell.

Introduction of the vectors into suspension cell was carried out by suspending the suspension CHO cell ($4\times10^6$ cells) in 400 μl of PBS buffer and co-transfecting the anti-human CD98 antibody expression transposon vector comprising the modified type puromycin resistance gene in the form of circular DNA (10 μg) and the pCAGGS-T2TP (20 μg) directly by electroporation.

In this case, the Tol2 transposase expression vector pCAGGS-T2TP was also introduced directly in the form of circular DNA in order to transiently express Tol2 transposase.

The electroporation was carried out using an electroporator (Gene Pulser Xcell system (manufactured by Bio-Rad)) under conditions of voltage of 300 V, electrostatic capacity of 500 μF and room temperature and using a cuvette of 4 mm in gap width (manufactured by Bio-Rad).

After the gene introduction by electroporation, the cells in each cuvette were inoculated onto one 96-well plate and cultured for 3 days in a $CO_2$ incubator using a CD OptiCHO medium (Invitrogen) supplemented with 5% soybean hydrolyzate.

Next, from the medium exchange after 2 days of the gene introduction, culturing was carried out for 4 weeks while adding puromycin (P9620, Sigma-Aldrich) to give a final concentration of 5 μg/ml and carrying out the medium exchange to the puromycin-containing medium at intervals of one week.

After the culturing, expression level of the antibody was determined using LANCE(R) assay (Perkin-Elmer Corp) by a sandwich method to which FRET (fluorescence resonance energy transfer) was applied. The results are shown in Table 2.

TABLE 2

| | Antibody producing cells | |
|---|---|---|
| | E (Modification 1) | F (Modification 2) |
| Antibody expression level (mg/L) of cells showing maximum expression | 1.0 | 2.2 |
| Average antibody expression level (mg/L) of top 10 cells | 0.7 | 1.6 |

As shown in Table 2, the antibody producing cell F which expresses the modified type puromycin resistance gene 2 showed two times or more antibody productivity of the antibody producing cell E which expresses the modified type puromycin resistance gene 1.

Example 5

Antibody Production by Antibody Producing CHO Cell which Expresses Modified Type Puromycin Resistance Gene 2

The antibody producing cell F obtained in Example 4 which expresses the modified type puromycin resistance gene 2 was cultured using a conical flask to produce anti-human CD98 antibody.

Specifically, the antibody producing cell F was expansion-cultured using 96-well plate, 24-well plate and 6-well plate in that order. Two cell lines of the antibody producing cell F in which the number of cell was sufficiently increased (cell line 1 and cell line 2) were selected, and respectively suspended in 35 ml of the CD OptiCHO medium (Invitrogen) supplemented with 5% soybean hydrolyzate so as to give a cell density of $2\times10^5$ cells/ml and cultured for 1 week on a shaker using a 125 ml capacity of conical flask (with a bent cap, Corning Glassworks) in an atmosphere of 37° C. and 5% $CO_2$, thereby producing the anti-human CD98 antibody.

Amount of the antibody in the medium after culturing was determined by HPLC (Waters Associates, Inc.). The results are shown in Table 3.

TABLE 3

| | Cell line 1 | Cell line 2 |
|---|---|---|
| Antibody expression level (mg/l) | 15.6 | 14.8 |

The above results show that in the suspension CHO cell, the antibody gene inserted between a pair of transposon sequences and the modified type drug resistance gene are introduced efficiently into the host chromosome and also are effective for the selection of a high expression cell. In addition, it was found that the thus obtained cell can be expansion-cultured and production of the protein of interest under a suspension culturing condition is possible.

Reference Example (1) Preparation of Suspension CHO Cell

An adhesive CHO-K1 cell EC85051005 (European Collection of Cell Cultures) which had been cultured using α-MEM medium (Invitrogen) containing 10% serum (FCS) was peeled off by a trypsin treatment and then recovered, followed by shaking culture at 37° C. in a 5% $CO_2$ incubator using the fresh the α-MEM medium containing 10% FCS.

Several days thereafter, growth of these cells was confirmed and then shaking culture was carried out by inoculating them into a α-MEM medium containing 5% FCS at a concentration of 2×10$^5$ cells/ml followed by shaking culture.

Further several days thereafter, the inoculation was similarly carried out using the α-MEM medium containing 5% FCS. Finally, a cell adapted to the suspension culture was prepared by repeating the sub-culturing and shaking culture using the serum-free α-MEM medium and confirming that the cells have the same growing ability as the case of their culturing in the presence of serum.

While the present invention has been described in detail and with reference to specific embodiments thereof, it will be apparent to one skill in the art that various changes and modifications can be made therein without departing from the spirit and scope thereof. This application is based on the Japanese patent application (No. 2010-279850), filed on Dec. 15, 2010, the entire contents of which are incorporated hereinto by reference.

INDUSTRIAL APPLICABILITY

According to the method for producing the protein of the present invention, a protein of interest can be efficiently produced using a mammalian cell. The cell of the present invention can be used as a protein producing cell for producing a recombinant protein.

SEQUENCE LISTING

SEQ ID NO:1—Description of Artificial sequence; Nucleotide Sequence of Non-autonomous Tol2 Transposon
SEQ ID NO:2—Description of Artificial sequence; Tol2-L sequence
SEQ ID NO:3—Description of Artificial sequence; Tol2-R sequence
SEQ ID NO:7—Description of Artificial sequence; Nucleotide Sequence of Wild Type of Neomycin Resistant Gene
SEQ ID NO:8—Description of Artificial sequence; Amino Acid Sequence encoded by Wild Type of Neomycin Resistant Gene
SEQ ID NO:9—Description of Artificial sequence; Nucleotide Sequence Modified Type of Neomycin Resistant Gene
SEQ ID NO:10—Description of Artificial sequence; Amino Acid Sequence of Synthetic Construct
SEQ ID NO:11—Description of Artificial sequence; Nucleotide Sequence of Modified Type of Neomycin Resistant Gene
SEQ ID NO:12—Description of Artificial sequence; Amino Acid Sequence of Synthetic Construct
SEQ ID NO:13—Description of Artificial sequence; Nucleotide Sequence of Modified Type of Neomycin Resistant Gene
SEQ ID NO:14—Description of Artificial sequence; Amino Acid Sequence of Synthetic Construct
SEQ ID NO:15—Description of Artificial sequence; Nucleotide Sequence encoding Anti-Human CD98 Antibody Heavy Chain Variable Region
SEQ ID NO:16—Description of Artificial sequence; Amino Acid Sequence of Synthetic Construct
SEQ ID NO:17—Description of Artificial sequence; Nucleotide Sequence encoding Anti-Human CD98 Antibody Light Chain Variable Region
SEQ ID NO:18—Description of Artificial sequence; Amino Acid Sequence of Synthetic Construct
SEQ ID NO:19—Description of Artificial sequence; Nucleotide Sequence of Wild Type of Puromycin Resistance Gene
SEQ ID NO:20—Description of Artificial sequence; Amino Acid Sequence encoded by Wild Type of Puromycin Resistance Gene
SEQ ID NO:21—Description of Artificial sequence; Nucleotide Sequence of Modified Type of Puromycin Resistance Gene
SEQ ID NO:22—Description of Artificial sequence; Amino Acid Sequence of Synthetic Construct
SEQ ID NO:23—Description of Artificial sequence; Nucleotide Sequence of Modified Type of Puromycin Resistance Gene
SEQ ID NO:24—Description of Artificial sequence; Amino Acid Sequence of Synthetic Construct
SEQ ID NO:25—Description of Artificial sequence; Nucleotide Sequence of Modified Type of Puromycin Resistance Gene
SEQ ID NO:26—Description of Artificial sequence; Amino Acid Sequence of Synthetic Construct
SEQ ID NO:27—Description of Artificial sequence; Nucleotide Sequence of Modified Type of Zeocin Resistance Gene
SEQ ID NO:28—Description of Artificial sequence; Amino Acid Sequence of Synthetic Construct
SEQ ID NO:29—Description of Artificial sequence; Nucleotide Sequence of Modified Type of Zeocin Resistance Gene
SEQ ID NO:30—Description of Artificial sequence; Amino Acid Sequence of Synthetic Construct
SEQ ID NO:31—Description of Artificial sequence; Nucleotide Sequence of Modified Type of Hygromycin Resistance Gene
SEQ ID NO:32—Description of Artificial sequence; Amino Acid Sequence of Synthetic Construct
SEQ ID NO:33—Description of Artificial sequence; Nucleotide Sequence of Modified Type of Hygromycin Resistance Gene
SEQ ID NO:34—Description of Artificial sequence; Amino Acid Sequence of Synthetic Construct

The invention claimed is:

1. A method for producing a protein of interest, comprising: introducing an expression vector which comprises a gene fragment comprising a DNA encoding the protein of interest, an attenuated selectable marker gene, and a pair of transposon sequences at both terminals of the gene fragment, into a suspension mammalian cell;
   integrating the gene fragment comprising the DNA encoding the protein of interest inserted between the pair of transposon sequences into a chromosome of the mammalian cell;
   obtaining a mammalian cell which expresses the protein of interest; and
   suspension-culturing the mammalian cell,
   wherein the pair of transposon sequences originate from medaka fish,
   wherein the attenuated selectable marker gene has a nucleotide sequence that is modified such that its expression level in the suspension mammalian cell is lowered, and wherein the attenuated selectable marker gene comprises a nucleotide sequence selected from the group consisting of SEQ ID NOs: 9, 11, 13, 21, 23, 25, 27, 29, 31 and 33.

2. A method for producing a protein of interest, comprising the following steps (A) and (B):
   (A) a step of simultaneously introducing the following expression vectors (a) and (b) into a suspension mammalian cell; integrating a gene fragment inserted between a pair of transposon sequences into a chromosome of the mammalian cell by a transiently expressed transposase; and obtaining a suspension mammalian cell which expresses the protein of interest:
      (a) an expression vector which comprises the gene fragment comprising a DNA encoding the protein of interest and an attenuated selectable marker gene and also comprises the pair of transposon sequences at both terminals of the gene fragment,
      (b) an expression vector which comprises a DNA encoding the transposase which recognizes the transposon sequences and has activity of transferring the gene fragment inserted between the pair of transposon sequences into the chromosome,
   (B) a step of suspension-culturing the suspension mammalian cell which expresses the protein of interest to produce the protein of interest,
   wherein the pair of transposon sequences originate from medaka fish,
   wherein the attenuated selectable marker gene has a nucleotide sequence that is modified such that its expression level in the suspension mammalian cell is lowered, and wherein the attenuated selectable marker gene comprises a nucleotide sequence selected from the group consisting of SEQ ID NOs: 9, 11, 13, 21, 23, 25, 27, 29, 31 and 33.

3. The method according to claim 1 or 2, wherein the suspension mammalian cell is a cell capable of surviving and proliferating in a serum-free medium.

4. The method according to claim 1 or 2, wherein the suspension mammalian cell is any one of the cells selected from the group consisting of a suspension CHO cell in which a CHO cell is adapted to suspension culture, an immortalized human embryonic retinoblast cell line, a rat myeloma cell YB2/3HL.P2.G11.16Ag.20 and a suspension mouse myeloma cell NS0 adapted to suspension culture.

5. The method according to claim 4, wherein the CHO cell is selected from the group consisting of CHO-K1, CHO-K1SV, DUKXB11, CHO/DG44, Pro-3 and CHO-S.

6. The method according to claim 1 or 2, wherein the pair of transposon sequences are nucleotide sequences originated from a pair of transposons which functions in a mammalian cell.

7. The method according to claim 1 or 2, wherein the pair of transposon sequences have nucleotide sequences that are originated from a pair of Tol2.

8. The method according to claim 7, wherein the nucleotide sequences originated from the pair of Tol2 have the nucleotide sequence of SEQ ID NO:2 and the nucleotide sequence of SEQ ID NO:3.

9. The method according to claim 1 or 2, wherein the pair of transposon sequences have nucleotide sequences that are originated from a pair of Tol1.

10. The method according to claim 9, wherein the nucleotide sequences originated from the pair of Tol1 have the nucleotide sequence of SEQ ID NO:35 and the nucleotide sequence of SEQ ID NO:36.

* * * * *